United States Patent
Khait et al.

(10) Patent No.: US 9,980,628 B2
(45) Date of Patent: May 29, 2018

(54) METHODS AND SYSTEMS FOR CONTROLLING AN ON/OFF SWITCH

(71) Applicant: GIVEN IMAGING LTD., Yoqneam (IL)

(72) Inventors: Semion Khait, Tiberias (IL); Oren Rosenberg, Kiryat Ono (IL)

(73) Assignee: Given Imaging Ltd., Yoqneam (IL)

( * ) Notice: Subject to any disclaimer, the term of this patent is extended or adjusted under 35 U.S.C. 154(b) by 388 days.

(21) Appl. No.: 14/652,155

(22) PCT Filed: Dec. 8, 2013

(86) PCT No.: PCT/IL2013/051008
§ 371 (c)(1),
(2) Date: Jun. 15, 2015

(87) PCT Pub. No.: WO2014/102768
PCT Pub. Date: Jul. 3, 2014

(65) Prior Publication Data
US 2015/0305595 A1     Oct. 29, 2015

Related U.S. Application Data

(60) Provisional application No. 61/747,548, filed on Dec. 31, 2012.

(51) Int. Cl.
*A61B 1/00* (2006.01)
*A61B 1/04* (2006.01)
*H04B 5/00* (2006.01)

(52) U.S. Cl.
CPC ...... *A61B 1/00006* (2013.01); *A61B 1/00036* (2013.01); *A61B 1/041* (2013.01); *H04B 5/0037* (2013.01)

(58) Field of Classification Search
None
See application file for complete search history.

(56) References Cited

U.S. PATENT DOCUMENTS

| 7,419,468 B2 | 9/2008 | Shimizu et al. |
| 7,834,725 B2 | 11/2010 | Pizzuto |

(Continued)

FOREIGN PATENT DOCUMENTS

| JP | 2002185628 | 6/2006 |
| JP | 2009119109 | 6/2009 |

(Continued)

OTHER PUBLICATIONS

"M24LR04E-R Datasheet", XP055230880, www.st.com (Jun. 2012).

*Primary Examiner* — Jared Fureman
*Assistant Examiner* — Joel Barnett
(74) *Attorney, Agent, or Firm* — Pearl Cohen Zedek Latzer Baratz LLP

(57) ABSTRACT

A control circuit for controlling a state of a switching circuit may include a first unit to sense and interpret a wireless signal or physical parameter as an "on" signal to transition the switching circuit to the "on" state, or as an "off" signal to transition the switching circuit to the "off" state, and to transfer a first digital signal or logic value and/or a second digital signal or logic value, which may respectively or combinatorially represent the "on" signal or the "off" signal, to a second unit via a first output and/or a second output of the first unit, respectively. The second unit may force a control input of the switching circuit to a logic value which is a function of the first digital signal or value and/or second digital signal or value and congruent with the state to which the switching circuit is to be transitioned.

17 Claims, 12 Drawing Sheets

(56) References Cited

U.S. PATENT DOCUMENTS

| | | | |
|---|---|---|---|
| 2001/0051766 A1 | 12/2001 | Gazdzinski | |
| 2005/0273170 A1* | 12/2005 | Navarro | A61F 2/442 623/17.13 |
| 2007/0129602 A1 | 6/2007 | Bettesh et al. | |
| 2008/0009671 A1* | 1/2008 | Kimoto | A61B 1/00036 600/109 |
| 2008/0076965 A1 | 3/2008 | Yoshizawa et al. | |
| 2009/0093690 A1* | 4/2009 | Yoshizawa | A61B 1/00016 600/300 |
| 2009/0099418 A1* | 4/2009 | Kimoto | A61B 1/00036 600/118 |
| 2010/0171596 A1* | 7/2010 | Burke | G06K 19/0717 340/10.4 |
| 2012/0262560 A1 | 10/2012 | Nisani et al. | |
| 2014/0104982 A1 | 4/2014 | Berg et al. | |
| 2014/0316193 A1* | 10/2014 | Taniguchi | A61B 1/00034 600/103 |
| 2015/0157195 A1* | 6/2015 | Iwaisako | A61B 1/00009 600/109 |

FOREIGN PATENT DOCUMENTS

| | | |
|---|---|---|
| JP | 2009285465 | 12/2009 |
| JP | 2010233692 | 10/2010 |
| JP | 201118882 | 9/2011 |
| WO | WO 2006095420 | 9/2006 |
| WO | WO 2013/000110 | 1/2013 |

\* cited by examiner

US 9,980,628 B2

METHODS AND SYSTEMS FOR CONTROLLING AN ON/OFF SWITCH

CROSS-REFERENCE TO RELATED APPLICATIONS

This application is a National Phase Application of PCT International Application No. PCT/IL2013/051008, entitled "METHODS AND SYSTEMS FOR CONTROLLING AN ON/OFF SWITCH", International Filing date Dec. 8, 2013, published on Jul. 3, 2014 as International Publication No. WO 2014/102768, which claims the benefit of U.S. Provisional Application No. 61/747,548, filed Dec. 31, 2012.

FIELD OF THE INVENTION

The present invention generally relates to switching circuits for switching systems (e.g., in-vivo sensing capsules, endoscopy capsules, etc.) "on" and "off", and more specifically to methods and systems for controlling the state of an on/off switch of systems.

BACKGROUND

In-vivo measuring systems are known in the art. Some autonomous capsule like in-vivo devices, which traverse the gastrointestinal (GI) system, may include an imaging sensor, or imager, for imaging (e.g., capturing images or taking pictures of) the interior of the GI system. An in-vivo device may include sensors of other types (e.g., pH sensor, pressure sensor, temperature sensor, motion sensor, etc.), and/or various types of tools (e.g., micro electro-mechanical system, or "MEMS"), for example to perform surgical operations in vivo and/or to administer medication in the GI system, for example from a container contained in an in-vivo device.

Swallowable in-vivo devices may not accommodate a manually-operated on/off switch because such devices typically are air-tight and sealed and, in any case, they typically cannot be operated manually once swallowed. Nevertheless, quality control standards may require that each device be tested prior to use, which may require that the device be activated and deactivated, possibly several times, for testing purposes prior to use, and an in-vivo device must be switched "off" while not in use (in order to preserve its battery's energy), and "on" just before swallowing it.

Reed switches are commonly used, in some cases in conjunction with other devices, to activate and deactivate in-vivo devices prior to use. Reed switches are, by nature, sensitive to electromagnetic ("EM") fields and may either be in "close" state or in "open" state when exposed to an EM field. Some reed switches may be sensitive to mechanical shock that may have an unwanted effect on the devices they activate/deactivate, for example, during transfer and handling of the devices. Reed switches may undesirably be activated by EM interference, for example by EM fields that may be used to maneuver the devices, or by random EM interference. In other cases, the electrical contacts of a reed switch may sometimes get stuck mechanically and, in such cases, it would not function properly, if at all.

While switching an in-vivo device on and off is beneficial, there are some drawbacks associated with conventional on/off switching schemes. It would be beneficial to have an on/off switching scheme for in-vivo devices, which overcomes the drawbacks described above.

SUMMARY OF THE INVENTION

An on/off switching mechanism is provided, which facilitates electromagnetic interference free control of "on" and "off" states of a device or system (e.g., swallowable in-vivo devices).

The on/off mechanism described herein typically controls major components of the device, e.g., an imager, illumination sources, and transmitter to transmit in-vivo data, and may be controlled by a circuit which is not initially (when in an off state) operating, or unpowered. E.g., embodiments of the circuit described herein may be part of a device such as an imaging capsule, and the circuit may be unpowered, or not operating, when the on/off mechanism is off.

The on/off switching mechanism included in or used by a device or system (for example in/by a swallowable in-vivo device) may include a control circuit and a switching circuit. The switching circuit may include a power input terminal that may be connected to a power source, a power output terminal that may be connected to electrical loads, and a switch control input via/through which the control circuit may control transitions of the switching circuit between an "on" state, in which the power input terminal is electrically connected to the power output terminal (to thereby power up the electrical loads), and an "off" state, in which the power input terminal is electrically disconnected from the power output terminal (to thereby disconnect the electrical loads from the power source). Transitioning of the switching system to a certain state (e.g., "on" or "off") may depend on the logic value (e.g., "0" or "1") of/at the switch control input (e.g., "1").

The control circuit may include a first unit and a second unit. The second unit may functionally/electrically be interposed between the first unit and the switching circuit. The first unit may sense a wireless signal (e.g., by using radio antenna) and/or physical parameter (e.g., by using a pressure sensor, temperature sensor, motion sensor, accelerometer, etc.), interpret the sensed wireless signal and/or physical parameter as an "on" signal to transition the switching circuit to the "on" state, or as an "off" signal to transition the switching circuit to the "off" state, and transfer a first digital signal or logic value or a second digital signal or logic value, or both signals or values to the second unit via a first output and/or a second output of the first unit, respectively. The first digital signal or logic value and the second digital signal or logic value may respectively or combinatorially (jointly) represent, or be congruent with, the "on" state/signal/command or the "off" state/signal/command "Respectively" refers to an embodiment where one of the digital signals (or one of the logic values) is congruent with the "on" state (e.g., used as a command to transition the switching circuit to the "on" state), and the other digital signal (or logic value) is congruent with the "off" state (e.g., used as a command to transition the switching circuit to the "off" state). "Combinatorially" refers to an embodiment where a combination of the first and second digital signals (or logic values) is used to transition the switching circuit to the "on" state, and a different combination of the first and second digital signals (or logic values) is used to transition the switching circuit to the "off" state. For example, the first combination may include a first digital signal that may be, or have, a certain logic value (e.g., "1") and a second digital signal that may be a clock pulse (or a pulse's rising, or pulse's falling, edge), and the second combination may include a first digital signal that may be a different logic value (e.g., "0") and a second digital signal that may be a clock pulse (or a pulse's rising, or pulse's falling, edge).

In some embodiments, the second unit may include a controller and a logic unit. In other embodiments, the second unit may include a flip-flop (e.g., D-FF). The second unit may set or force the (switch) control input of the switching circuit to a logic value which is a function of the first digital signal and/or second digital signal congruent with the state to which the switching circuit is to be transitioned. The first unit may transfer the first digital signal or logic value or the second digital signal or logic value, or both signals/values, to the second unit using a wired communication protocol, for example the IIC ($I^2C$) communication protocol.

The first unit may be or include a "communication and energy harvesting ("CEH") unit, and the second unit may be or include a control and logic unit ("CLU"). The CEH unit may include a receiving unit for sensing, for example, radio frequency ("RF") signals and/or a physical parameter, a first output terminal that the CEH unit may controllably set to a voltage +V (V>0 volt) every time the CEH unit harvests electrical energy from RF signals (or another type of signals) or physical parameter sensed via the receiving input, and a second output terminal that the CEH unit may controllably transition from a 'high-Z' state (high impedance state) to a zero volt state (or low impedance state, or 'low-Z' state), for example, whenever the CEH unit is internally writing data into a local/internal register.

The CLU may include two binary inputs, referred to herein as "set" input and "reset" input, and one binary output. The CLU's "reset" input may functionally be connected to the second output (e.g., the "high-Z/zero,low-Z" terminal) of the CEH unit. The second output of the CEH unit, by being connected to the CLU's "reset" input, may control the logic state (e.g., "0"/"1") of the CLU's logic output. The CLU's logic output may functionally be connected to the switch control input of the switching circuit in order to control the "on/off" state of the switching circuit.

The first output of the CEH unit (the output settable to 0 v or to +V, V>0 volt) may, in some embodiments, also be functionally connected (e.g., logically OR-ed) to the switch control input of the switching circuit (e.g., it may be logically OR-ed with the CLU's output) in order to control the "on/off" state of the switching circuit. If either one of the OR-ed signals (CLU's output or the first output of the CEH unit), or both signals, has (have) a certain predetermined logic value (e.g., "1"), the switching circuit may be transitioned from the "off" state to the "on" state, or remain in the "on" state, in order to electrically connect the power source to the device or system that are to be powered up. Otherwise (both OR-ed signals do not have the certain predetermined logic value; e.g., both of them have the logic value "0"), the switching circuit may be transitioned from "on" state to "off" state, or remain in the "off" state, and disconnect the power source from the device or system.

The CEH unit may be configured to wirelessly communicate, for example over a RF communication channel, with a remote, wireless, switch activation system. The CEH unit may be configured to receive, for example, a first RF signal from the remote switch activation system corresponding to "on" command, and to respond to the received first signal by (i) disconnecting its second output (which is connected to the "reset" input terminal of the CLU), for example by forcing it to be in the high-Z state, and, concurrently or after some delay, (ii) enabling its first output (which is functionally connected to the input terminal of the switching circuit) and setting it to high voltage, +V, that may represent logic level/state "1", in order to set the switching circuit to the "on" state. During the "on" state of the switching circuit, the CLU may be powered up by the power source, in which case the CLU's "set" input, and consequently, its output, transitions to logic value/state "1". Since, in some embodiments, the CLU's logic output is connected to the switch control input of the switching circuit, transitioning its state to logic value/state "1" maintains the "on" state of the switching circuit, and, therefore, a self-sustained power loop.

The CEH unit may be configured to receive, for example, a second RF signal from the remote switch activation system corresponding to "off" command, and to respond to the received second RF signal by transitioning its second output (which is connected to the "reset" input of the CLU) from the high-Z state to the zero, or low-Z state, to thereby force the CLU to set its output to logic value "0". When the CEH unit's second output transitions to logic value/level "0", the switching circuit's state may change from "on" to "off" (assuming that the CEH's first output connected to an input terminal of the switching circuit, which was at logic value "1", has already transitioned to logic value "0", for example by the CEH disabling its first output, or by the waned/ decreased energy which was (previously) harvested by the CEH).

According to another example embodiment, the first output of the CEH unit ($V_{OUT}$) may functionally be connected to a first input of the CLU (e.g., data in), and the second output of the CEH unit (e.g., "high-Z/zero,low-Z" terminal) may functionally be connected to a second input of the CLU (e.g., clock input). The output of the CLU may functionally be connected to the switch control input of the switching circuit and manipulated by the digital signals or logic values simultaneously provided by the CEH unit's two outputs to the CLU's two inputs, to thereby control the state of the switching circuit.

In some embodiments, the CLU may be implemented as a digital flip-flop ("FF") including two inputs and one output. In these embodiments, the first output of the CEH unit (e.g., a $V_{OUT}$ terminal) may functionally be connected to a data (D) input of the FF, and the second output of the CEH unit (e.g., a "high-Z/zero,low-Z" terminal) may functionally be connected to a clock (CLK) input of the FF in order to control the state (e.g., logic level "0" or "1") of the FF's output (Q) based on the logic state ("0" or "1") existing at the D input. The FF's output (Q) may functionally be connected to the switch control input of the switching circuit in order to control the "on/off" state of the switching circuit.

The CEH unit may be configured to receive, for example, over a RF communication channel, a first RF signal from the remote system corresponding to "on" command, and to respond to the received "on" command by setting its first output to high voltage +V (+V corresponds to, or embodies, logic level "1") in order to set the data (D) input of the FF to logic value "1" and, optionally, to power up the CEH unit and the FF. While powered up, the CEH unit may use its second output to transfer a clock pulse to the CLK input of the FF to, thereby, set the FF's output (Q) to correspond to the logic level/state of the FF's D input (e.g., "1"). Setting the FF's output Q to logic bit "1" may transition the switching circuit from "off" state to "on" state in which the switching circuit may connect the power source to electrical loads (e.g., the CEH unit and/or the FF device, and possibly other electrical loads; e.g., in-vivo device or system).

During the switching circuit's "on" state, the CEH unit may receive, for example, a second RF signal from the remote system corresponding to "off" command, and respond to the received "off" command by disabling its first output in order to set the FF's D input to logic value "0", and by changing the state of its second output (which is functionally connected to the FF's CLK input) from high-Z to zero, or low-Z state, to thereby set the FF's output (Q) to the logic level/state corresponding to the logic value/state of the FF's D input (e.g., "0"). Setting the FF's output Q to logic level "0" may transition the switching circuit from the "on" state to the "off" state. The flip-flop may be a "D" type flip-flop (D-FF) or a latch.

The CEH unit may be or include a radio frequency identification ("RFID") tag or device, the first output of the RFID tag/device may be an Energy Harvesting ("EH") terminal that may internally be connected to an energy harvesting unit and be enabled to output a DC voltage which is harvested wirelessly, for example, from RF transmissions (or the EH may be disabled to prevent this from happening), and the second output of the RFID tag/device may be a "RF-BUSY/WIP" terminal of the RFID device that may be configurable to operate in a "RF-BUSY" mode of operation in which it may transition from high-Z state to zero voltage, or low-Z state whenever the RFID senses a RF signal, in order to indicate (e.g., to an external device) that the RFID tag/device is busy handling an incoming (sensed) RF signal, or in a WIP ("Write in Progress") mode of operation in which it transitions from high-Z state to zero voltage, or low-Z state whenever the RFID tag/device internally writes data in a local register, in order to indicate (e.g., to an external device) that the RFID tag/device is busy writing data internally.

The first digital signal or logic value may comprise or embody energy harvested from the sensed wireless signal or sensed physical parameter, and the second digital signal or logic value may comprise, or be, a signal indicative of internal data writing in the RFID tag/device.

In one embodiment of the invention, a controller of the CLU may be a controller controlling an in-vivo device/sensor or system, the "set" input of the CLU may be the controller's own power input (+VCC), the output terminal of the CLU may be connected to a register bit which is configured to have logic value "1" when the controller is powered up and logic value "0" when the controller receives a reset signal, and the "reset" input of the CLU may be connected to a register bit which is configured to receive the reset signal.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION OF THE INVENTION

The description that follows provides various details of exemplary embodiments. However, this description is not intended to limit the scope of the claims but instead to explain various principles of the invention and the manner of practicing it.

Figure 1A:
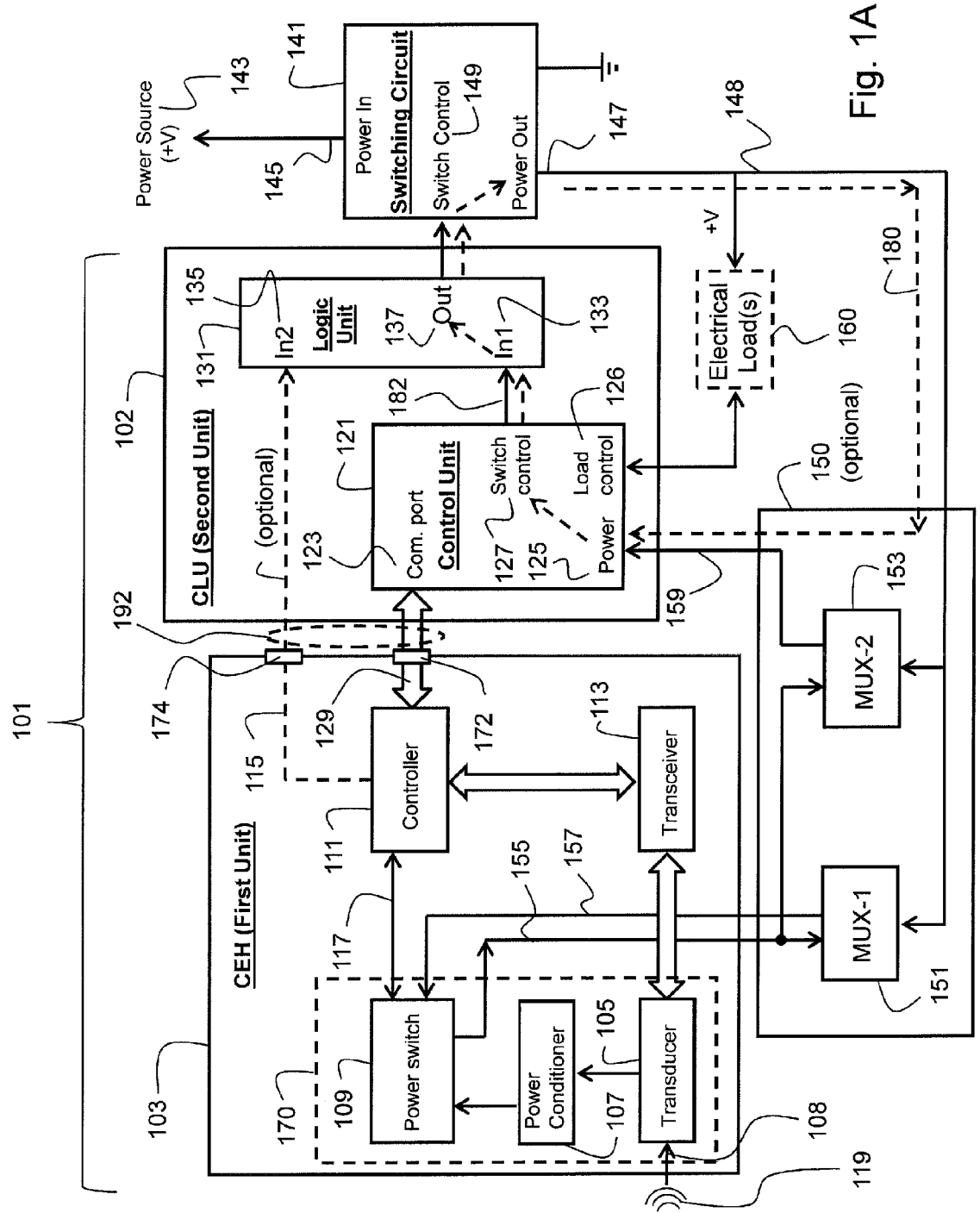
FIG. 1A is a general diagram of a switch control system according to the present invention.

FIG. 1A is a general diagram of a switch control system (control circuit) 101 for controlling a switch according to the present invention. Switch control circuit 101 may include a first unit 103, for example a communication and energy harvesting (CEH) unit 103. CEH unit 103 may include a transducer 105. Transducer 105 may include a receiver or transmitter, or both receiver and transmitter for receiving and/or transmitting (108) RF signals (119), or other types of wireless signals (119) (e.g., visible light, invisible light, etc.). Transducer 105 may alternatively or additionally include one or more sensors for sensing physical parameter(s) 119 (e.g., temperature, pressure, motion, etc.). Transducer 105 may be configured to convert received, or sensed, wireless signal or physical parameter into electrical energy (e.g., voltage). Transducer 105 may be part of an energy harvesting (EH) circuit 170 that is configured to harvest energy from received, or sensed, signals, from, or by utilizing, the electrical energy (e.g., voltage) that transducer 105 may output. EH circuit 170 may also include a power conditioner 107 to condition the transducer's output energy, and a controllable power switch 109 that may be controlled (e.g., by controller 111) to distribute conditioned energy/power internally (inside CEH unit 103) and/or externally (to device(s) or system(s) outside CEH 103). Power conditioner 107 may include, for example, a voltage step-up circuit (e.g., voltage doubler, etc.), a voltage step-down circuit, capacitors, coils, controller, switches, filter(s), etc., to obtain one or more supply voltages.

CEH unit 103 may also include a transceiver 113. Transceiver 113 may functionally be connected to transducer 105 and configured to receive therefrom and process a signal in order to interpret/identify it as either a command/signal to switch switching circuit 141 "on", or as a command/signal to switch switching circuit 141 "off". Transceiver 113 may transfer a message to a controller 111, notifying controller 111 of the "on" command/signal or "off" command/signal, depending on the type of the signal received or sensed by transducer 105.

Switch control circuit 101 may also include a second unit, for example control and logic unit (CLU) 102, which may include a control unit 121 and a logic unit 131. CLU 102 (control unit 121) may have a communication input ("Com. port", shown at 123) connected via communication bus 129 to output port 172 of CEH unit 103. CLU 102 (logic unit 131) may have a logic output ("Out", shown at 137) connected to a switch control input 147 of switching circuit 141. CLU 102 may exchange messages with CEH unit 103. CEH unit 103 (e.g., by using controller 111) may transfer a first digital signal, or logic value, and a second digital signal, or logic value, to CLU 102 via two output ports 174 and 172, respectively, or via one port (e.g., port 172). The first and second digital signals, or logic values, may respectively or combinatorially (jointly, or in conjunction) represent, or be congruent with, for example, an "on" signal or command to transition switching circuit 141 to "on" state in which switching circuit 141 may, for example, connect power source/supply 143 to the "Power out" output 147 of switching circuit 141, or an "off" signal or command to transition switching circuit 141 to "off" state in which switching circuit 141 may, for example, disconnect power source/supply 143 from "Power out" output 147 of switching circuit 141. Output ports 172 and 174 may be part of, or constitute, a single/common communication channel (192) via which CEH 103 may transfer the first and second digital signals to CLU 102 using a protocol which may be compatible with, for example, the Inter-Integrated Circuit (IIC, or $I^2C$) interface. Briefly, the IIC, generically referred to as "two-wire interface", is a multi-master serial, single-ended, computer bus that is used to connect low-speed peripherals to an electronic device (e.g., controller).

CLU 102 (e.g., one of control unit 121 and logic unit 131 or both units) may respond to the first and second signals, or logic values, it receives via ports 172 and 174 by outputting to the switching circuit's input (switch control input 149), via the "Out" output 137, a logic signal/value that may transition switching circuit 141 to the switching state according to or as per the signal/command represented by the first signal or logic value, or by the second signal or logic value, or by a combination of the first and second signals, or values, which is/are congruent with the state to which switching circuit 141 is to be transitioned. The way the first and second signals, or logic values, are generated by CEH 103 and used by CLU 102 to control the state, or state transition, of switching circuit 141, is described in more detail below.

Controller 111 may respond to the message/command it receives from transceiver 113 by transferring, via a first output (e.g., communication port 172 and communication bus 129), a first signal (or more than one signal) to input 123 of control unit 121, and, optionally, a second signal 115 to a logic unit 131 via a second output (e.g., output 174). Controller 111 may force the first signal and/or the second signal to have a logic value such that the first signal or the second signal, or a combination thereof, may cause, trigger, initiate or commence transition of switching circuit 141 from "off" state, in which switching circuit 141 disconnects power source 143 which is connected to its "Power In" input 145 from its "Power Out" output 147, to "on" state, in which switching circuit 141 connects power source 143 to "Power Out" output 147. When power source 143 is connected, via/by switching circuit 141, to "Power out" terminal 147, the power source may initially power up, for example, electrical load(s) 160 and/or other devices or systems (e.g., CEH unit 103 and/or CLU 102 (e.g., control unit 121)). Alternatively, controller 111 may respond to the message/command it receives from transceiver 113 by transferring both signals (e.g., the first and the second signals) to control unit 121 via a common output (e.g., output 172) and a common communication bus (e.g., communication bus 129).

In one implementation of switch control circuit 101, CEH unit 103 may have one output port (e.g., output port 172) via which controller 111 unit 103 may exchange messages with, and/or transfer the first and second signals to, control unit 121, via communication buss 129, by using any suitable communication protocol (e.g., IIC or another wired protocol). In this implementation, the first and second signals are used for both transitioning switching circuit 141 to the "on" state and to the "off" state, as described below. For example, controller 111 may transfer the first signal or logic value and the second signal or logic value, via communication channel 129, to control unit 121, and control unit 121 may interpret or identify the first and second signals transferred from controller 111, respectively or combinatorially, as, or congruent with, an "on" signal (assuming switching circuit 141 is to be transitioned from the "off" state to the "on" state), or as an "off" signal (if switching circuit 141 is to be transitioned from the "on" state to the "off" state). Control unit 121 may receive the first and second signals from the CEH unit's port 172 via communication port 123 ("Com. port").

Control unit 121 may have a first output 127 ("Switch control") that may functionally be connected to a first input 133 ("In1") of a logic unit 131 and may be used to control the state of switching circuit 141. Control unit 121 may also have a second output 126 ("Load control") that may functionally be connected to one or more electrical loads (e.g., a camera system), and may be used by control unit 121 to exchange messages with these loads. Control unit 121 may respond to the first and second signals it receives from CEH unit 103 via input "Com. port" (123) by outputting, via the control unit's "Switch control" output (127), a corresponding logic signal (e.g., "on" or "off" signal) to the logic unit's input port "In1" (133). In response to the logic signal that logic unit 131 receives at its input port "In1" (133), logic unit 131 may output, via its "Out" output 137, a control signal to the "Switch Control" input 149 of switching circuit 141, to, thereby, cause switching circuit 141 to change its state from "off" to "on" (if it is in the "off" state and the CEH's first signal, or second signal, or a combination thereof, designates or represents an "on" command/signal), or vice versa (if it is in the "on" state and the CEH's first signal, or second signal, or a combination thereof, designates or represents an "off" command/signal).

In the above described implementation, the first signal that control unit 121 may receive from controller 111 (via output 172) may be or may represent a logic value required to transition switching unit 121 either to "on" state or to "off" state, and the second signal that control unit 121 may receive from controller 111 (also via output 172) may cause control unit 121 to output, via the "Switch control" output 127, a logic value that matches the logic value represented by the first signal. For example, the first signal may represent logic value "1", but control unit 121 may respond to it (e.g., also set its "Switch control" output 127 to that logic value) only if control unit 121 interprets the second signal as a command to set/force its output 127 to the logic value represented by the first signal. The second signal required to set/force the control unit's output 127 to the logic value of the first signal may include, or be consisted of, a clock pulse, a signal rising-edge (a signal transitioning from "0" to "1"), or a signal falling-edge (a signal transition from "1" to "0").

When a signal or physical parameter 119, which is received by transducer 105, is interpreted by transceiver 113 as, for example, an "on" command (e.g., a command to change the state of switching circuit 141 to "on"; i.e., the state in which power source 143 is connected to "Power out"

output 147), controller 111 may force the first signal to have a first logic value (e.g., "1"), and the second signal to have a value (e.g., "1"), or a logic transition (e.g., rising edge), to set the controller unit's output 127 to a value matching that of the first signal (to thereby transition switching circuit 141 to the "on" state).

When a signal or physical parameter 119, which is received by transducer 105, is interpreted by transceiver 113 as, for example, an "off" command (e.g., a command to change the state of switching circuit 141 to the state in which power source 143 is disconnected from the "Power out" output 147), controller 111 may force the first signal to have a second logic value (e.g., "0", if its previous logic level was "1"), and the second signal to have a value (e.g., "1"), or a transition (e.g., rising edge), to set the controller unit's output 127 to a value matching that of the first signal (to thereby transition switching circuit 141 to the "off" state).

When switching circuit 141 connects power source 143 to "Power out" output 147, control unit 121 may be powered up (159), via multiplexer MUX-2. As a result of this, "Switch control" output 127 of control unit 121 may be forced to have a logic value (e.g., "1") that continues to force (182) logic unit 131 to output (137) the logic value required by switching circuit 141 to connect power supply 143 to "Power out" output 147. Accordingly, connecting power source 143 to "Power out" output 147 by switching circuit 141 may result in a self-sustained 'power loop' 180 that is maintained until CEH 103 receives a signal 119 that it interprets as a command to transition switching circuit 141 back to the "off" state.

In a second implementation of switch control circuit 101, controller 111 may transfer the first signal (e.g., "1"), via a first output (e.g., output 174), to a second input 135 (input "In2") of logic unit 131, and the second signal (e.g., a "reset" signal), via a second output (e.g., output 172), to the "Com. port" input 123 of control unit 121. In this implementation, one signal (e.g., the first signal) may be used to transition switching circuit 141 to the "on" state, and the other signal (e.g., the second signal) may be used to transition switching circuit 141 to the "off" state, as described below. (Other implementations may be used.).

When a signal or physical parameter 119, which is received by transducer 105, is interpreted by transceiver 113 as an "on" command (e.g., a command to change the state of switching circuit 141 to the state in which power source 143 is connected to the "Power out" output 147), controller 111 may enable output 174 and transfer the first signal (e.g., logic value "1") to input "In2" 135 of logic unit 131 to, thereby, cause logic unit 131 to output (137) a logic value that may cause switching circuit 141 to connect power source 143 to "Power out" 147. As described above, for example in connection with the first implementation, when switching circuit 141 transitions to the "on" state, power loop 180 sustains itself via output signal 182 that control unit 121 outputs via its "Switch control" output 127.

When/while switching unit 141 is in the "on" state and a signal or physical parameter 119 received by transducer 105 is interpreted by transceiver 113 as an "off" command, controller 111 may disable output 174 of CEH 103 and transfer the second signal to input 123 of control unit 121 to reset its "Switch control" output 127 (e.g., set its logic value to "0"). Resetting output 127 while output 174 is disabled may cause switching circuit 141 to disconnect power source 143 from "Power out" 147, and, consequently, to disconnect power loop 180. (Control 111 may alternatively disable output 174 shortly after power loop 180 sustains itself via logic input "In1" (133) of logic unit 131, or before the signal or physical parameter 119 interpreted by transceiver 113 as the "off" command is received or sensed.) Control unit 121 and logic unit 131 may, therefore, jointly interpret the first and second signals transferred from controller 111 respectively or combinatorially as an "on" signal (assuming switching circuit 141 is to be transitioned from the "off" state to the "on" state), or as an "off" signal (assuming switching circuit 141 is to be transitioned from the "on" state to the "off" state).

Switch control circuit 101 may also include an external power distribution ("EPD") unit 150. EPD unit 150 may include a first multiplexer 151 (which is designated as "MUX-1"), and a second multiplexer 153 (which is designated as "MUX-2". When switching circuit 141 is turned on, or transitioned to the "on" state" (for example), it may provide voltage supply 148 to MUX-1 and MUX-2. MUX-1 and MUX-2 may also be provided with voltage supply form CEH unit 103, as shown at 155.

Each of MUX-1 (151) and MUX-2 (153) may include a controller, or a logic circuit, to manage the power sources, and to determine which power supply (e.g., the power supply 148 provided by power source 143 via switching circuit 141, and/or the voltage supply (155) provided by CEH unit 103) is to be provided to which device (e.g., to CEH unit 103, as shown at 157, and/or to control unit 121, as shown at 159). Such determination may be based, for example, on the state of switching circuit 141, and/or on the voltage level of each voltage supplier, and/or on the electrical load of the devices that need to be powered up at any given time, etc.). For example, when switching circuit 141 connects power source 143 to EPD unit 150, to provide voltage/power 148, a logic circuit embedded in MUX-1 may determine to power up (157) CEH unit 103 by using power source 143 rather than CEH unit 103; e.g., by using power switch 109, and a logic circuit embedded in MUX-2 may also determine to power up (159) control unit 121 by using power source 143 rather than using, for example, power switch 109 of CEH unit 103. In another example, when switching circuit 141 disconnects power source 143 from its output 147, MUX-1 and MUX-2 may determine to connect a voltage supply generated by EH circuit 170 back to CEH unit 103 (as shown at 157) and/or to control unit 121 (as shown at 159).

Figure 2:
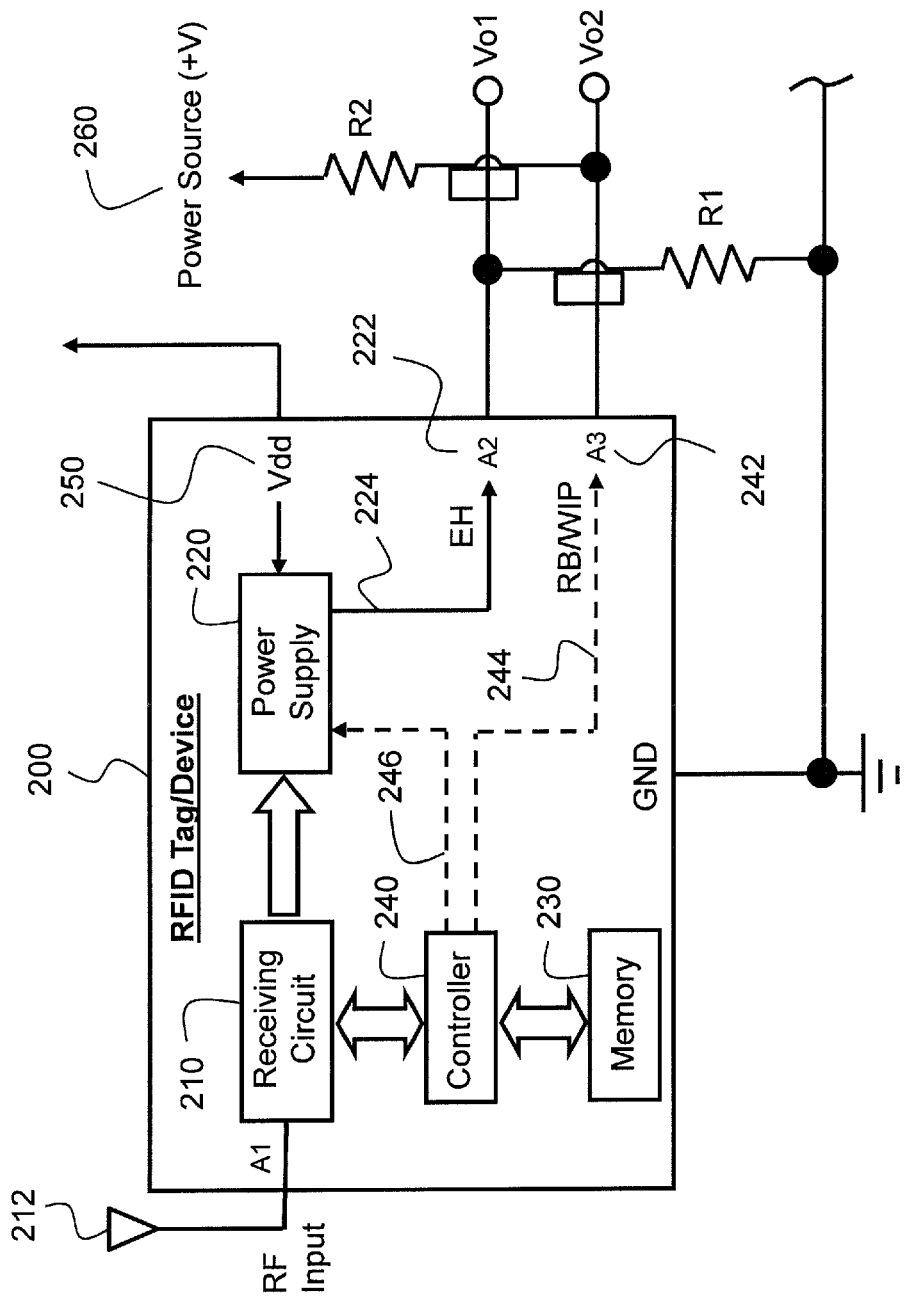
FIG. 2 is a schematic block diagram of an example RFID device according to a second embodiment of the present invention.
Figure 3:
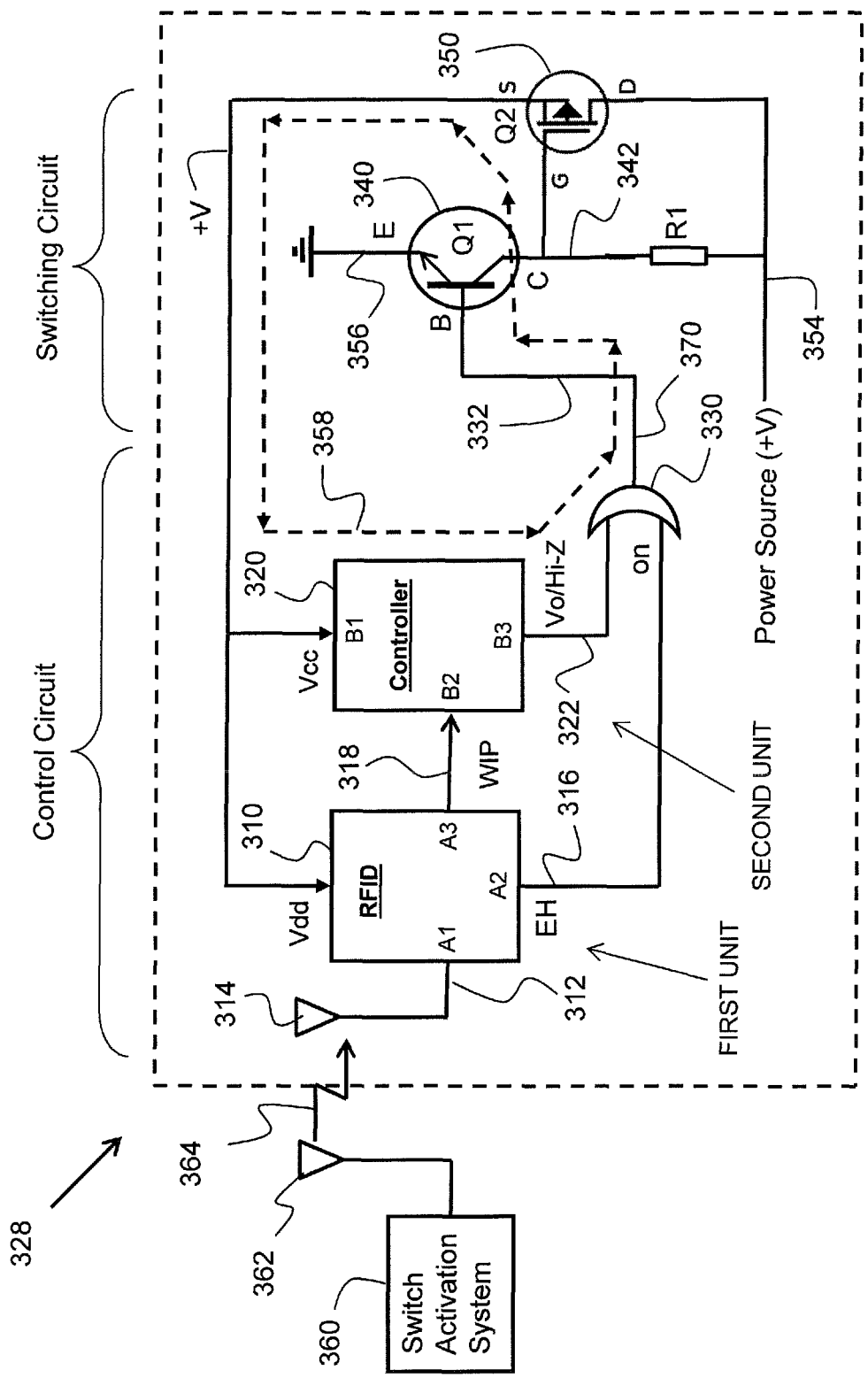
FIG. 3 shows an example implementation of the first embodiment.
Figure 4:
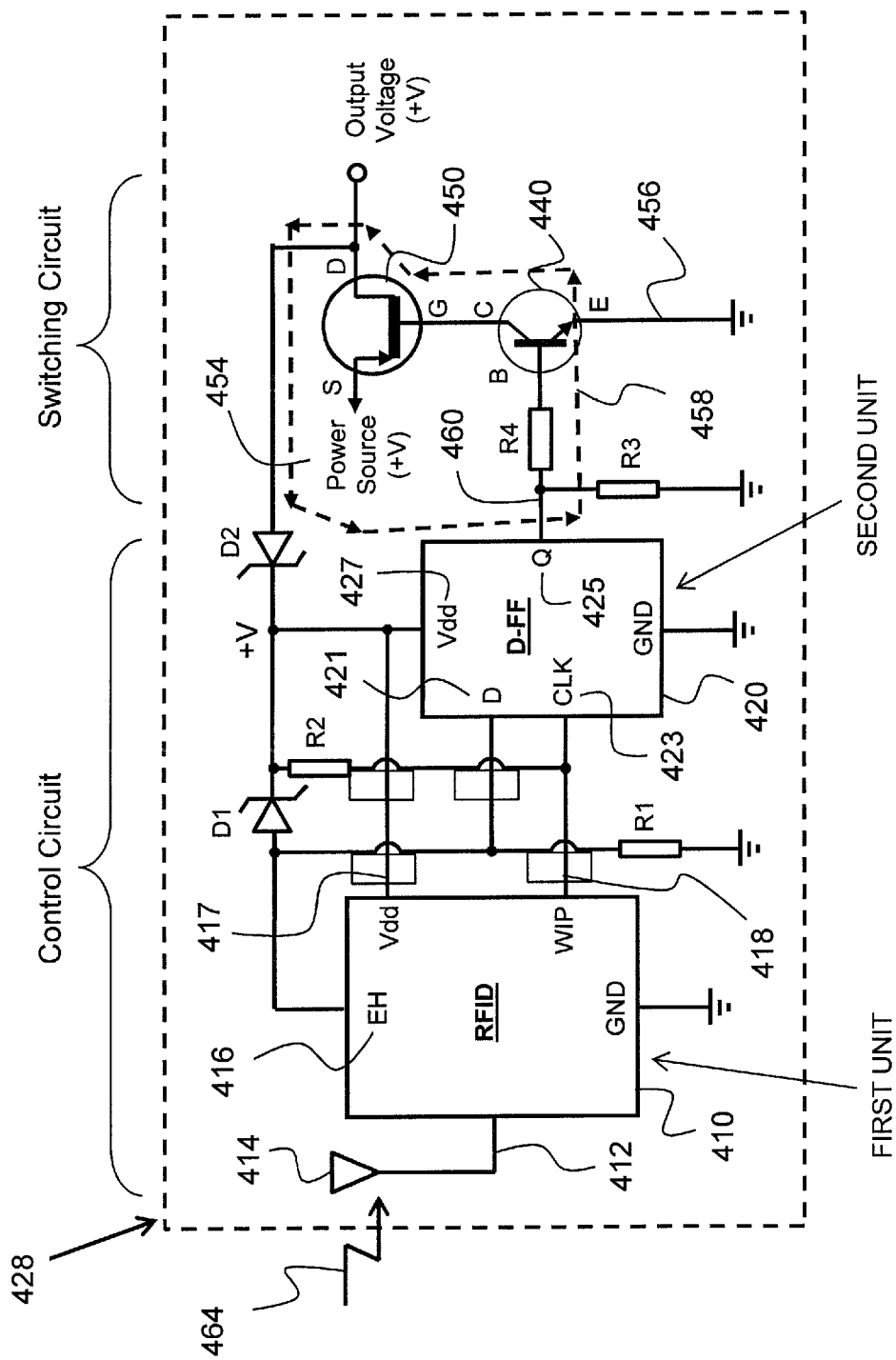
FIG. 4 shows an example implementation of the second embodiment.

CEH 103 may be implemented, for example, as a RFID device, as demonstrated, for example, by FIGS. 2-4. Control unit 121 may be implemented, for example, as a controller device, as demonstrated, for example, by FIG. 3, or as a D-FF device as demonstrated, for example, by FIG. 4. Control unit 121 may be a controller of, or residing in, for example, an in-vivo sensing device (e.g., in-vivo imaging capsule). In such a case, the imaging capsule's controller may transfer various data and information types (e.g., capsule's identification and/or type and/or version, sensing data; e.g., pressure, temperature or motion data) to CEH 103 by using the bi-directional communication bus 129, and CEH 103 may include a transmitter (not shown in FIG. 1A) that may transmit the data and information to an external or remote system, for example to the remote system switching the capsule on and off (by means of switching circuit 141). For example, a capsule may transmit a feedback signal to the external system, for example that the capsule has been switched "on", by using a controller that may function in the same way, or in a similar way, as control unit 121. Control unit 121 may generally be any memory device with suitable logic circuit. Logic unit 131 may be, for example, a logic OR gate, as shown, for example, in FIG. 3. EPD 150 may be optional. When switching circuit 141 is in the "on" state, power source 143 may power either, or both, CEH unit 103 and control unit 121 as a default, or exclusively. The switching system and methodology described in connection with FIG. 1A may be incorporated into or embedded in a device such as a swallowable in-vivo imaging, or otherwise sensing, capsule as shown, for example, in FIG. 5. The first and second units of FIG. 1A may be implemented in various ways, some of which are described below in connection with the related drawings.

Figure 1B:
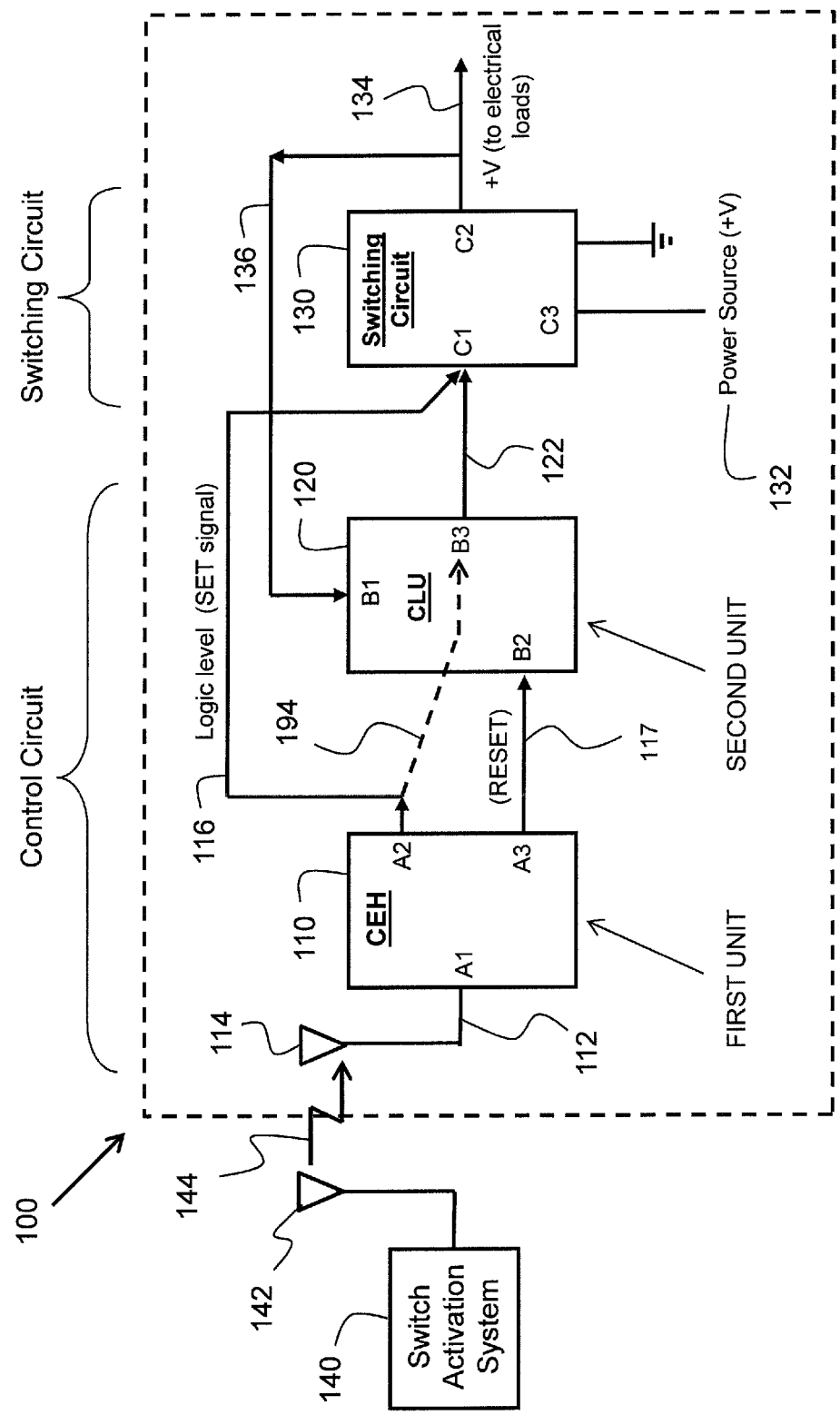
FIG. 1B is a block diagram of a switch control system according to a first embodiment of the present invention.
Figure 1C:
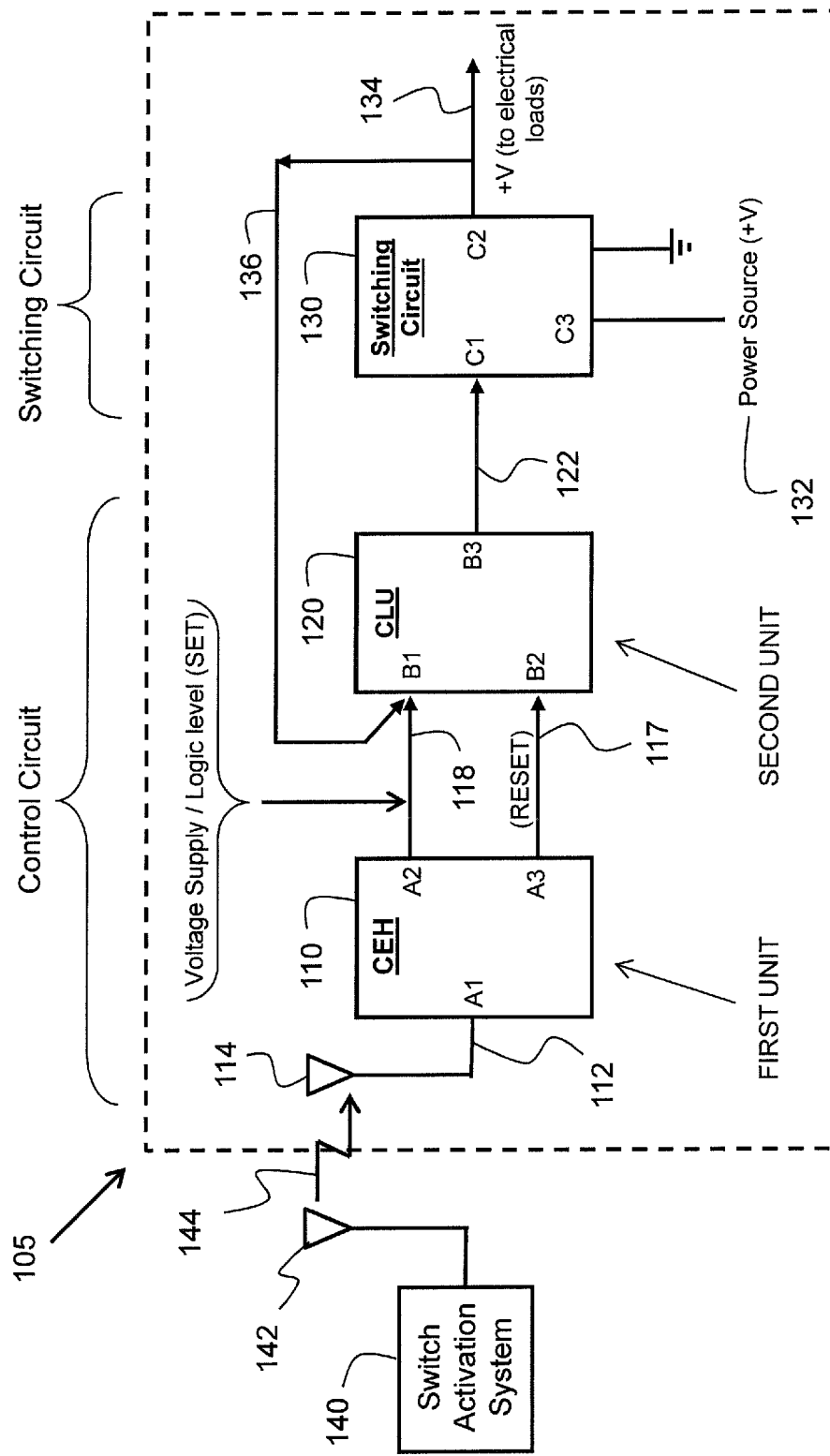
FIG. 1C is a block diagram of a switch control system according to a second embodiment of the present invention.

FIG. 1B is a block diagram of a switch control system 100 according to a first embodiment of the present invention. On/off switching circuit 100 may include a CEH unit 110, as an example first unit, and a CLU 120, as an example second unit. CEH unit 110 may have a RF input A1 functionally connected to a RF antenna 114, a first output A2 functionally directly (116), or indirectly (194), connected to a control (logic) input C1 of a switching circuit 130, and a second logic output A3 functionally connected to a logic input B2 of CLU 120. CLU 120 may have a logic output B3 functionally connected to control input C1 of switching circuit 130. Output A2 of CEH unit 110 may, at times, output a voltage supply to power up external devices (e.g., CLU 120, see FIG. 1C). Output A2 may output (e.g., at other times) a logic value/level "0" or "1" to control input C1 of switching circuit 130 (as schematically illustrated in FIG. 1B) or to CLU 120 (as schematically illustrated in FIG. 1C). Output A3 of CEH unit 110 may output a logic level to input B2 of CLU 120 to thereby affect the logic output at terminal B3 of CLU 120, and, consequently, the logic state of switching circuit 130. Input terminal B1 of CLU 120 may receive power for powering CLU 120, as demonstrated, for example, in FIG. 1B, or it may be a logic input terminal receiving a logic value/level from output A2 of CEH unit 110, as demonstrated, for example, in FIG. 1C.

Switching circuit 130 may be in one of two states ("on" or "off"), the actual state depending on the logic value/level at its control input C1. If the logic value at control input C1 is "1", switching circuit 130 may be at the "on" state in which switching circuit 130 may connect CLU 132 to its power output C2 and output power source 132 to power up 134 an electrical circuit (load) and also CLU 120, as shown at 136. CLU 120 may be configured such that when it is powered up (via input B1), output B3 is set to (it is forced to) logic value/level "1". Setting output terminal B3 to logic level "1" may trigger a self-sustained power loop (136, 122).

Transitions from "off" state to "on" state, and vice versa, of switching circuit 130 may be controlled, for example, by a remote switch activation circuit 140. Switch activation circuit 140 may be external to the device containing switching circuit 100. Switch activation circuit 140 may include a RF transceiver that may be configured to transmit data (e.g., identification data, messages, control data, etc.) and to receive data. Depending on the functionality of CEH unit 110, CEH unit 110 may include only a RF receiver or both RF receiver and RF transmitter.

Switching circuit 130 "on": in the "off" state, CEH unit 110, CLU 120 and switching circuit 130 receive no power, and power source 132 is disconnected from output C2 of switching circuit 130. In order to transition switching circuit 130 from the "off" state to the "on" state (e.g., to switch "on" an in-vivo device, or another device or system which may be operated using on/off switching circuit 100), switch activation system 140 may use an antenna 142 to transmit a RF signal 144 to CEH unit 110 (e.g., to a circuit similar to circuit 105 of FIG. 1A) to transition switching circuit 130 to the "on" state, as described below. CEH unit 110 may receive RF signal 144 via antenna 114, and respond to it by setting output A2, hence control input C1 of switching circuit 130, to logic level "1". Switching circuit 130 may respond to the logic level "1" (a "set" command) at control input C1 by connecting, or transferring, the power source 132 connected to its input C3 to its output C2. When power source 132 is connected or transferred to output C2 of switching circuit 130, power source 132 powers up (136) CLU 120 via input B1. As described above, when input B1 is energized (receives power), output B3 is set to logic level "1". Consequently, the power loop (136, 122) is maintained. (Output A2 of CEH unit 110 may be configured to be at logic value "1" momentarily, yet long enough to enable output terminal B3 to stabilize at the logic level "1", after which the power loop (136,122) sustains itself.

Switching circuit 130 "off": in order to switch the in-vivo device "off", the power loop (136, 122) described above has to be disconnected. Disconnecting power loop (136, 122) may be performed, for example, by forcing output B3 of CLU 120 to logic value/state "0". Disconnecting the power loop (136, 122) may be performed by switch activation system 140 transmitting another ("off") RF signal 144 to CEH unit 110 via antennas 142 and 114, to transition switching circuit 130 to the "off" state, as described below.

CEH unit 110 may receive the "off" RF signal 144, via antenna 114, and respond to it as follows: if output A2 continues to output logic value "1" during the "on" state of switching circuit 130, CEH unit 110 may disable (e.g., disconnect) output A2. In addition, CEH unit 110 may forward to input B2 of CLU 120, via output A3, a resetting/"off" signal (e.g., clock pulse, pulse's rising or falling edge), in response to which CLU 120 may set its output B3 to logic level "0". CLU 120 may respond to the reset/"off" signal it receives from output A3 of CEH unit 110 by forcing its output B3 to logic level "0". As described above, transitioning the logic level of output B3 of CLU 120 from "1" to "0" disconnects the power loop (122, 136) and, consequently, transitions switching circuit 130 from the "on" state to the "off" state. The switching system and methodology described in connection with FIG. 1B may be incorporated into or embedded in a device such as a swallowable in-vivo imaging, or otherwise sensing, capsule shown, for example, in FIG. 5.

FIG. 1C is a block diagram of a switch control system 105 according to a second embodiment of the present invention. The second embodiment may be similar to the first embodiment shown in FIG. 1B except that output A2 of CEH unit 110 may functionally be connected (118) to input terminal B1 of CLU 120, rather than to control input C1 of switching circuit 130. In this embodiment, switching circuit 130 may be switched "on" when output A2 of CEH unit 110 outputs (118) a voltage supply to power up CLU 120 via input B1. When powered up, CLU 120 may set output B3 to logic level "1" to initiate a sustainable power loop (122, 136). Switching circuit 130 may be switched "off" by disabling output A2 (to prevent unintentional "on" state occurrences) and transferring a reset signal 117, via output A3, to input B2 of CLU 120. With the disablement of output A2 of CEH 110, reset signal 117 forces output B3 of CLU 120 to logic value "0", to thereby disconnect the self-sustained power loop (122, 136). The switching system and methodology described in connection with FIG. 1C may be incorporated into or embedded in a device such as a swallowable in-vivo imaging, or otherwise sensing, capsule shown, for example, in FIG. 5.

Figure 1D:
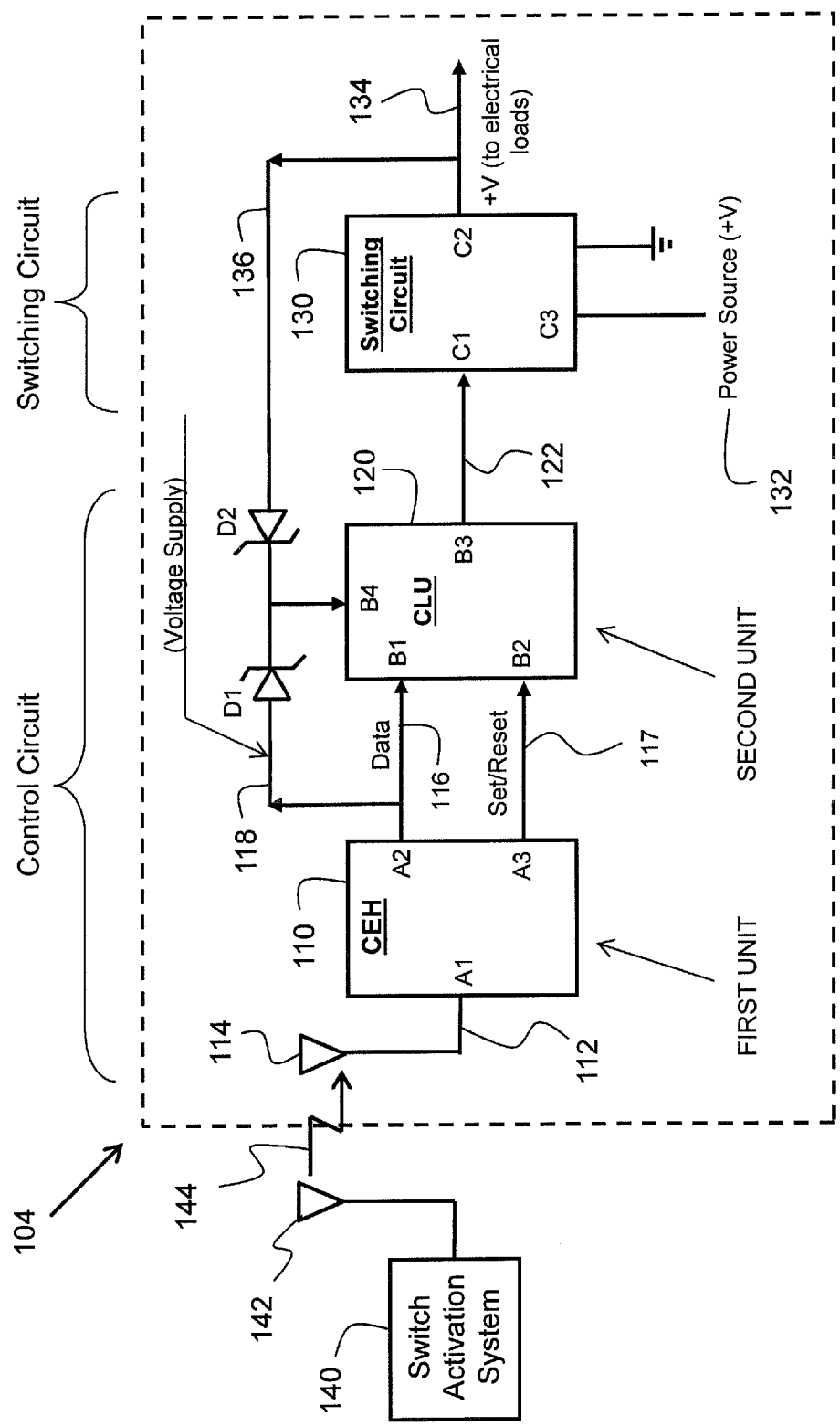
FIG. 1D is a block diagram of a switch control system according to a third embodiment of the present invention.

FIG. 1D is a block diagram of a switch control system 104 according to a third embodiment of the present invention. Transitioning switching circuit 130 from "off" state to "on"

state may be performed as described below. In this embodiment, output A2 of CEH unit 110 may be used both as a power providing output, to power up (118) CLU 120 (via diode D1) and as a binary bit, or logic value, providing output, to provide a data bit or logic value (116) to input B1 of CLU 120. CEH unit 110 may forward to input B2, via output A3, a "set" signal (117) to cause CLU 120 to set output B3 to a logic value which is identical to the logic value at input B1 at the time the "set" signal is provided to input B2. If a "set" signal is provided to input B2 when input B1 is at logic level "1", forwarding a "set" signal to input B2 results in setting output B3 to logic level "1" and, consequently, in transitioning switching circuit 130 to the "on" state. When switching circuit 130 is in the "on" state, power source 132 is connected to output C2 of switching circuit 130 and powers (136) CLU 120 via diode D2. In order to transition switching circuit 130 from "on" state to "off" state, the data bit 116 provided to input B1 of CLU 120 has to be set to logic value "0", and a "reset" signal (117) may have to be concurrently provided to input B2 in order to force output B3 of CLU 120 to the logic value of input B1, which, in this case, is "0". (A logic value "0" at output B3 disconnects the power loop (122, 136) and results in transitioning switching circuit 130 to the "off" state.) The switching system and methodology described in connection with FIG. 1D may be incorporated into or embedded in a device such as a swallowable in-vivo imaging, or otherwise sensing, capsule shown, for example, in FIG. 5.

FIG. 2 is a schematic diagram of a RFID tag or device 200. RFID tags, in general, may include features that, if manipulated properly, may render them suitable to function, for example, as the CEH unit 110 shown, for example, in FIGS. 1A-1D. Typically, a RFID reader communicates with a RFID device through interrogation, meaning that the RFID reader transmits a signal that causes the RFID device to transmit desired information back to the RFID reader/interrogator. (Such information may include identification information of the RFID tag, information related to an article associated with the RFID tag, etc.) In addition to transmitting information from a RFID device to its interrogating RFID reader in response to an interrogation transmission, the RFID device internally generates various types of signals, some of which may be utilized by embodiments of the present invention (in conjunction with a complementary circuit) to transition on/off switching circuit (e.g., switching circuit 328 of FIG. 3) from "on" state or "off" state and vice versa. The way RFID signals are utilized for controlling a switching system is described below, for example in connection with FIGS. 3 and 4. Some embodiments of the present invention may not use the RFID tag's transmission capability to transmit information back to its RFID reader. For example, transmissions from a RFID device may be disabled or ignored. Alternatively, the RFID device may not include a transmitter that otherwise might be used to transmit responses to the RFID reader. In other embodiments, the RFID tag's transmission capability may be used, for example, to notify the RFID reader (e.g., capsule activation system 360 of FIG. 3) of the current switching state of on/off switching circuit 328 (for example), and therefore of the end device (e.g., capsule). The features that may make RFID 200 suitable to function as CEH unit 110, or in a similar way, are described below.

RFID tag 200 may include a receiving circuit 210 connected to a RF antenna for receiving RF signals transmitted from a RFID reader, which may be, or be included in, for example, a switch activation system similar to switch activation system 140 of, for example, FIG. 1B. A RFID device may include an internal power source, or not. In one embodiment assume that RFID device 200 does not include a power source. Receiving circuit 210 may include energy harvesting circuit (e.g., electrical coil(s), capacitor(s), etc.) for wirelessly harvesting energy from an external energy source for powering up RFID device 200. RFID device 200 may also include complimentary power supply circuit 220, which may, for example, store the harvested energy and may include a power distribution circuit and a power control circuit. RFID device 200 may also include a memory 230 for storing information (e.g., RFID tag's identification information, information related to an object that may be identifiable by RFID device 200, information/data that RFID device 200 may receive via RF antenna 212, etc.), and a controller 240 for controlling the various functions of RFID device 200.

RFID device 200 may also include an "Energy Harvesting" (EH) output terminal 222. Controller 240 may be configured, or receive a command (e.g., via RF antenna 212), to enable (246) a connection between an output 224 of power supply 220 and output (EH) 222, or to disable the connection. In the "enable" mode of operation, power supply 220 may output (224) a supply voltage (+V) to the EH output terminal 222 whenever receiving circuit 210 harvests energy from a received RF transmission. In the "disable" mode of operation, controller 240 may disconnect power supply 220 from output (EH) 222. Controller 240 may disconnect output terminal 222 (EH) from power supply 220 in order to prevent output terminal 222 (EH) from outputting a supply voltage (+V) or a logic level "1" when receiving circuit 210 receives RF signals which are not intended for RFID device 200, or whenever the logic state of output 222 should change from logic level/state "1" (e.g., voltage +V) to logic level "0", or remain in logic level/state "0".

RFID device 200 may also include a "RF-BUSY/WIP" (RB/WIP) output 242. RF-BUSY/WIP output 242 may be internally settable to a zero state, in which its voltage may be zero or approximately zero (logic level/state "0"), or to a high-Z state, in which the output may be electrically disconnected from the external circuit (e.g., resistor R2 in FIG. 2). The high-Z state, in conjunction with an external pull-up resistor (e.g., resistor R2), may be used to generate a logic level/state "1". In digital circuits, "high-Z" output (also known as "tri-stated output" or "floating output") refers to a circuit output that is not driven or forced to any defined logic level by the circuit; the signal in that output is neither driven to a logical high nor to low level, hence the term "tri-state". In analog circuits, a high impedance node is a circuit node that does not have any low impedance path to any other nodes. Therefore, a circuit output that is at the high-Z state can practically be regarded as an open circuit.

Controller 240 may be configured, or receive a command (e.g., via RF antenna 212) to configure (244) output RB/WIP 242 to operate either as a RF-BUSY output or as a WIP (Write in Progress) output. If RB/WIP output 242 is configured (244) to operate as a RF-BUSY output, its state may transition from the high-Z state to the zero state whenever receiving circuit 210 receives a RF communication. However, if RB/WIP output 242 is configured to operate as a WIP output, its state may transition from the high-Z state to the zero state only whenever controller 240 writes data into memory 230. For the purposes of embodiments of the present invention, RB/WIP output 242 is configured (244) to operate as a WIP output because using it as a RF-BUSY output might render the RFID device, and therefore, the switch activation system as a whole, susceptible to random RF noises. (A random RF signal might inadvertently/uncontrollably change the state of the RF-BUSY output, and this may interfere with the operation of the control system as a whole.) Configuring RB/WIP output 242 to operate as a WIP output, on the other hand, ensures that the state of output A3 (242) changes from high-Z state to zero state only after controller 240 writes data into memory 230. (Controller 240 writes data into memory 230 only after it processes the data and determines that it is intended to RFID device 200, and this ensures that random signals are ignored.)

RFID device 200 may have a power supply input terminal Vdd (250) for receiving power from an external power source (e.g., from power source 143 of FIG. 1A of from power source 132 of FIGS. 1B-1D) directly or indirectly; e.g., via a switching circuit such as switching circuit 130.

Using RFID device 200 as the CEH unit 103,110,310: RFID device 200 may be initialized such that output EH (terminal A2, at 222) is disabled, and RB/WIP output 242 is configured to operate as a WIP output. In operation, when RFID device 200 does not receive a RF transmission, it is de-energized, in which case EP (A2) output 222, hence circuit terminal, is at zero potential (corresponding to logic level "0"), and RB/WIP output 242 is at high-Z state. Since output RB/WIP 242 is connected to pull-up resistor R2, no electrical current flows through resistor R2 when output 242 is at high-Z state. Therefore, voltage +V of a power source 260 appears at terminal Vo2, and terminal Vo2 may be regarded as being at logic level "1". If a switch activation system transmits a RF transmission to RFID device 200 and controller 240 determines that the RF transmission is an "on" command that is intended for it, controller 240 connects output EH (222) to power supply 220 in order to output a supply voltage +V (to set terminal Vo1 to logic state "1") and writes data, which may be arbitrary, into memory 230. When controller 240 writes data into memory 230, the state of output 242 changes from high-Z to zero (low-Z), and this changes the logic state of terminal Vo2 from "1" to "0".

In one embodiment since communication with RFID device 200 is implemented using RF transmission bursts, supply voltage +V may be supplied to output 222 (the logic state of output 222 may change to "1") only momentarily. (It may diminish after the RF transmission burst is over.) Likewise, when controller 240 is done writing the data into memory 230, output 242 resumes the high-Z state. The logic state transitions from "0" to "1" and from "1" to "0" at output 222 (which corresponds to output A2 in, for example, FIGS. 1B-1D) and the logic state transitions from "1" to "0" and from "0" to "1" at output 242 (which corresponds to output A3 of FIGS. 1B-1D) may be used to control a CLU (e.g., CLU 120) and/or a switching circuit (e.g., switching circuit 130) to transition the switching circuit to the "on" state. When the "on" command/signal transmission is exhausted (which results in the end device or system being switched "on"), RFID device 200 may continue to be energized (e.g., via an external power source connected to input 250 (Vdd)), output 222 may still be enabled or disabled, and output 242 may resume the high-Z state (terminal Vo2 may resume logic level "1").

When the switch activation system transmits a RF transmission to RFID device 200 and controller 240 determines that the RF transmission is an "off" command that is intended for it, controller 240 disconnects output EH (222) from power supply 220 in order to maintain, or set, terminal Vo1 to logic state "0". Controller 240 may additionally write another arbitrary data into memory 230 to thereby transition the state of output 242 from high-Z to zero or low-Z, in order to change the logic state of terminal Vo2 from "1" to "0". The logic state "0" at output 222 (which corresponds to output A2 of FIGS. 1B-1D) and the logic state transitions from "1" to "0" and from "0" to "1" at output 242 (which corresponds to output A3 of FIGS. 1B-1D) may be used to control a CLU (e.g., CLU 120) and/or a switching circuit (e.g., switching circuit 130) to transition the switching circuit to the "off" state. The switching system and "on"/ "off" signals' generating methodology described in connection with FIG. 2 may be incorporated into, embedded in or used by a device such as a swallowable in-vivo imaging, or otherwise sensing, capsule shown, for example, in FIG. 5.

FIG. 3 is a schematic diagram of an on/off switching circuit 328 according to another example embodiment. On/off switching circuit 328 may include a first circuit that may include, resemble, or be implemented as, a RFID device such as RFID device 310 (as an example first unit). RFID device 310 may have a RF input 312 that may functionally be connected to a RF antenna 314, a first output (EH) 316 that may functionally be connected to a first input of an OR logic gate 330, and a second output (WIP) 318 that may functionally be connected to an interrupt input of a controller 320, as an example second unit.

Output EH (316) may transition between "disabled" mode of operation, in which it is disconnected from the RFID's internal circuit (and, therefore, does not provide an output voltage), and "enabled" mode of operation, in which it is permitted to output a direct current ("DC") voltage in response to interrogation signals that capsule activation system 360 may transmit and RFID device 310 may sense/ receive (e.g., by antenna 314). (Capsule or device activation system 360 may be or include a RFID reader that may be configured to send "on" and "off" commands to RFID device 310 to commence an "on" session or an "off" session.) An RFID device may be active or passive. If RFID 310 is passive, a RFID reader system/station communicating with it (e.g., capsule activation system 360) may also power up RFID device 310 by using electromagnetic induction. The way the two modes, or two states, of output EH (316) and the WIP output 318 are used to control the state of a switch is described below.

Initializing switching circuit 328: initially, the output EH 316 of RFID device 310 is disabled in order to prevent RFID device 310 from unintentionally switch the capsule "on". (As explained above, disabling output EH 316 of RFID device 310 means that this output may be set (forced) to zero voltage.) Initially, the output 318 of RFID device 310 is configured to operate only in the WIP mode in order to assure that RFID device 310 is responsive only to transmissions intended for it (e.g., transmissions whose intention is to switch switching system 328 "on" or "off"), and not to other types of transmissions that should be ignored by RFID device 310.

Assume that switching circuit 328 is initially in the "off" state and, therefore, de-energized, meaning that no operation voltage is provided to the various circuits/loads of switching circuit 328. In the "off" state, the base (B) of transistor Q1 (340) receives no electrical current, for which reason transistor 340 is in cutoff state. Consequently, no electrical current flows through the collector (C) terminal of transistor 340, hence through pull-up resistor R1. Therefore, the battery's power 354, or most of it, appears at the collector (C) terminal of transistor 340. Consequently, power transistor 350 is also in cutoff state and, therefore, the "off" state of switching circuit 328 is maintained.

Switching circuit 328 "on": when a RFID device receives an interrogation signal from a RFID reader, the RFID tag responds to the interrogation signal by writing data in its internal registers. This feature, or capability, of the RFID device is used to set, configure or force output terminals of the RFID device to desired operational states, as described herein. (The data that the RFID device internally writes may be arbitrary because it is the writing operation itself, not the data, which is utilized to transition the switching circuit to the "on" state.)

When device activation system 360 interrogates (e.g., transmits an "on" command to) RFID device 310, output EH 316 of RFID device 310 is enabled and outputs a voltage +V, or any other signal corresponding to or representing logic level "1". In response to output EH 316 outputting the voltage +V, OR logic gate 330, which is connected to an input 370 of the switching circuit, outputs (332) logic level "1" to the base (B) input terminal of control transistor Q1 (340), to thereby cause transistor 340 to transition from cutoff state to conduction, or saturation, state. In the conduction state (or in the saturation state), control transistor 340 forces its collector (C) terminal, and hence, the gate (G) terminal of power transistor 350 to the zero, or near zero, potential (ground) 356. When gate G of power transistor 350 is forced to be at the zero or near zero potential (356), power transistor Q2 (350) transitions from cutoff state to conduction or saturation state. When power transistor 350 is in the conduction or saturation state, it connects battery's power 354, via transistor Q2, to the Vcc input (B1) of controller 320 to power up the controller. When controller 320 is powered up, it sets its output B3 (322) to voltage +V, or to any other signal corresponding to, or representing, logic level "1", and the logic level "1" is forwarded, via OR logic gate 330, to transistor 340 to maintain its conduction (or saturation) state. Consequently, power transistor 350 maintains its conduction or saturation state and continues to provide battery's power 354 to controller 320 to thereby maintain a self-sustained power loop 358. (Capsule activation system 360 may, at this stage, stop transmitting signals to RFID device 310 or be distanced away from it without disrupting power loop 358.)

Switching circuit 328 "off": in order to switch the in-vivo device "off, power loop 358 described above (which maintains the "on" state) has to be disconnected. Disconnecting the perpetual loop may be performed by capsule activation system 360 transmitting an "off" RF signal 364 to circuit 328, via antennas 362 and 314, to switch power switch 350 "off", as described below. When capsule activation system 360 'interrogates' RFID device 310 (this time it transmits an "off" command to RFID device 310), output EH 316 of RFID device 310 (e.g., the RFID device's energy harvesting terminal) is disabled and RFID device 310 writes data internally. As a result of the data writing by RFID device 310, the state of output 318 of RFID device 310 momentarily changes from high-Z to zero or low-Z. As a result of changing the state of output 318 from high-Z state to zero or low-Z, and since output 318 is connected to input B2 of controller 32, controller 320 forces output B3 (322) to zero state. As a result of disabling output EH 316 and changing the state of output 322 to zero, OR logic gate 330 outputs (332) logic value "0".

When output 332 of OR logic gate 330 transitions from logic level "1" to logic level "0", control switch 340 enters a cutoff state in which it provides (342) the battery's power (+V) 354 to the control gate (G) of power switch 350 instead of ground potential 356. As a result of the control switch's transition to the cutoff state, power switch 350 transitions from "on" state to (it resumes the) "off" state, thereby disconnecting the battery's power 254 from circuit 220 (and from other loads in the in-vivo device; e.g., controller 310). As a result of the transition of power switch 350 from the "on" state to the "off" state, output 322 of controller 320 remains low (at logic level "0", e.g., zero voltage or high-Z state) so that the output of logic OR 330 remains at logic level "0", the output 342 of control switch 340 continues to output the battery's power (+V) 245, and, consequently, power switch 350 maintains its "off" state, for example, until another "on" command is transmitted by/from capsule activation system 360 to RFID device 310. The switching system and methodology described in connection with FIG. 3 may be incorporated into or embedded in a device such as a swallowable in-vivo imaging, or otherwise sensing, capsule shown, for example, in FIG. 5.

FIG. 4 is a schematic diagram of an on/off switching circuit 428 according to another example embodiment. On/off switching circuit 428 may include a RFID device 410 (as an example first unit) that may function in a similar way as RFID device 310 of FIG. 3, and a 'D' type flip-flop ("D-FF") 420 that may combine the "on" and "off" functionality of controller 320 and OR logic device 330 of FIG. 3. On/off switching circuit 428 may also include a control switch 440 (as an example second unit) and a power switch 450 that may respectively function in a similar way as control switch 340 and a power switch 350 of FIG. 3. RFID device 410 may include a RF input 412 that may functionally be connected to a RF antenna 314 for receiving signals to transition the state of switching circuit 428 from "off" to "on", and vice versa. RFID device 410 may also include a first output (EH) 416 to output a greater than zero DC voltage every time RFID device 410 harvests energy while it receives an interrogation signal 464, for example, from a capsule activation system similar to system 360 of FIG. 3. RFID device 410 may also include a second output 418 (WIP). D-type flip-flop 420 may include a data input "D" (shown at 421) that may be functionally connected to the EH output port (416) of RFID device 410. Data input D (421) may receive control data bits (one control data bit at a time) from EH output port 416. D-FF 420 may also include a clock input terminal "CLK" (shown at 423), and an output port/terminal "Q" (shown at 425). Output port 425 may be functionally connected to an input (460) of the switching circuit. Assuming D-FF 420 is powered (e.g., its Vdd terminal, shown at 427, receives an operational voltage), any binary bit, "0" or "1", which is provided to D input 421 may be transferred to output terminal (Q) 425 when a clock pulse arrives at CLK input 423. That is, every time CLK terminal 423 is 'clocked' (it receives a clock pulse) by WIP output 418, the binary bit at the D terminal 421 is 'forwarded' to the D-FF's output Q shown at 425.

Initializing switching circuit 428: initially, the output EH 416 of RFID device 410 may be disabled in order to prevent RFID device 410 from unintentionally switching the capsule "on". (As explained above in connection with FIG. 3, which explanation is applicable to FIG. 4 as well, disabling output EH 316 of RFID device 310, and output EH 416 of RFID device 410, means that output EH 316 (and 416) is forced to zero voltage.) Initially, the output 418 of RFID device 310 may be configured to operate in the WIP mode in order to assure that RFID device 410 is responsive only to transmissions intended for it (e.g., transmissions whose intention is to switch switching system 428 "on" or "off"), and not to other types of transmissions that should be ignored by RFID device 410.

Assume that switching circuit 428 is initially in the "off" state and, therefore, de-energized, meaning that no operation voltage is supplied to the various circuits/loads of switching circuit 428. In the "off" state the Q output 425 of D-FF 420 is at logic level "0", for which reason base (B) of transistor 440 receives no electrical current and therefore transistor 440 is in cutoff state. Consequently, the gate (G) control input of power switch 450 is also in its cutoff state and, therefore, the "off" state of switching circuit 428 is maintained.

Switching circuit 428 "on": when a capsule activation system, for example one that is similar to capsule activation system 360, transmits an interrogation signal to RFID device 410, RFID device 410 harvests energy from the interrogation signal to power its circuits (during the energy harvesting process, output EH 416 outputs voltage +V, which corresponds to or represents logic level "1"). The voltage +V outputted by RFID device 410 is provided, through diode D1, to the Vdd input 417 of RFID device 410 and to the Vdd input 427 of D-FF 420, to power them up. Because the output EH 416 of RFID device 410 is functionally connected to the D input 421 of D-FF 420, the D input of D-FF 420 is also at logic level "1". If, during, or as a result of, the interrogation session RFID device 410 determines that the interrogation signal is intended to it, it starts writing data internally. As a result of the internal data writing by RFID device 410, WIP output 418 of RFID device 410 changes its output from high-Z state to logic level "0", and therefore (factoring in pull-up resistor R2 which is connected to the supply voltage provided by output EH 416) the logic state at the CLK input 423 changes from "1" to "0". Since WIP output 418 resumes the high-Z state (and the CLK input consequently resumes logic level "1") after the data writing is over, the data writing process causes the logic level sequence "1"→"0"→"1", which creates a pulse for the CLK terminal 423 of D-FF 420. In response to the pulse provided to the CLK input 425, the logic level "1" at the D-FF's D terminal 421 (which results from the energy harvesting during the interrogation process) is 'transferred' by D-FF 420 to its output 425 (Q).

Changing the state of output (Q) terminal 425 of D-FF 420 from the low logic state (logic level "0") to the high logic state (logic level "1") causes control switch/transistor 440 to transition from cutoff state to conduction, or saturation, state, in which control transistor 440 forces its collector (C) terminal, and therefore, the gate (G) terminal of power transistor 450 to the zero potential (ground) 456. In response to forcing the gate (G) of power transistor 450 to the zero potential 456, power transistor 450 transitions from cutoff state to conduction, or saturation, state in which it connects battery's power 454 to the Vdd terminals 417 and 427 of RFID device 410 and D-FF 420, respectively, to power them up. This powering up scheme guarantees that D-FF 420 (and, depending on the embodiments, also RFID device 410) are powered up also when RFID device 410 stops harvesting energy, for example because the RFID device/tag stops receiving interrogation signals. As long as D-FF 420 is powered up and RFID device does not receive a command to switch switching system 428 "off", the output 425 (Q) of D-FF 420 continues to be at the high logic state ("1") and, consequently, the battery's power 454 continues to be provided to D-FF 420 (and optionally to RFID device 410). (The capsule activation system communicating with RFID device 410 may, at this stage, stop transmitting signals 464 to RFID device 410 or be distanced away from it, and power loop 458 would still perpetuate via output 425 of D-FF 420.

Switching circuit 428 "off": in order to switch the in-vivo device "off, power loop 458 described above (which sustains the "on" state) has to be disconnected. Disconnecting power loop 458 may be performed by an interrogating system (e.g., system 360) transmitting another ("off") RF signal 464 to antenna 414 of circuit 428, to switch power switch 450 "off", as described below. When RFID device 410 is interrogated again (this time for commencing an "off" procedure by RFID device 410), the energy harvesting output EH 416 of RFID device 410 is disabled in order to change the logic state at the D input 421 from logic level "1" to logic level "0". (In this condition the power loop 458 still perpetuates because D-FF 420 is still powered up via diode D2 and its output 425 is still at logic state "1"). Power loop 458 may be disconnected, for example, by forcing output Q of D-FF 420 to logic state "0". Forcing output Q of D-FF 420 to zero may be done by sending another clock pulse to CLK input 423 of D-FF 420 while the new logic state (logic state "0") exists at the D input (input 421) of D-FF 420.

Generation of a new clock pulse for the D-FF by the RFID device is performed as described below. It is assumed that there is some minimal time period separating or between the time when RFID device 410 receives the command to switch switching system 428 "on" and the time when RFID device 410 receives the next command to switch switching system 428 "off". During this period, EH output 416 of RFID device 410 can, and therefore is, forced to zero volts/state, and, in addition, WIP output 418 is at a high-Z state, for which reason the logic level at CLK input 423 is "1". After the minimal time period is over, RFID device 410 may receive the "off" RF signal 464, via antenna 414, and respond to it by writing arbitrary data into a memory and, while writing is in progress, transitioning the state of WIP output 418 from high-Z state to zero or low-Z state. When the data writing process is over, RFID device 410 may transition WIP output 418 back from zero state, or low-Z state, to high-Z state, to thereby generate the pulse that is provided to CLK input 423.

Figure 5:
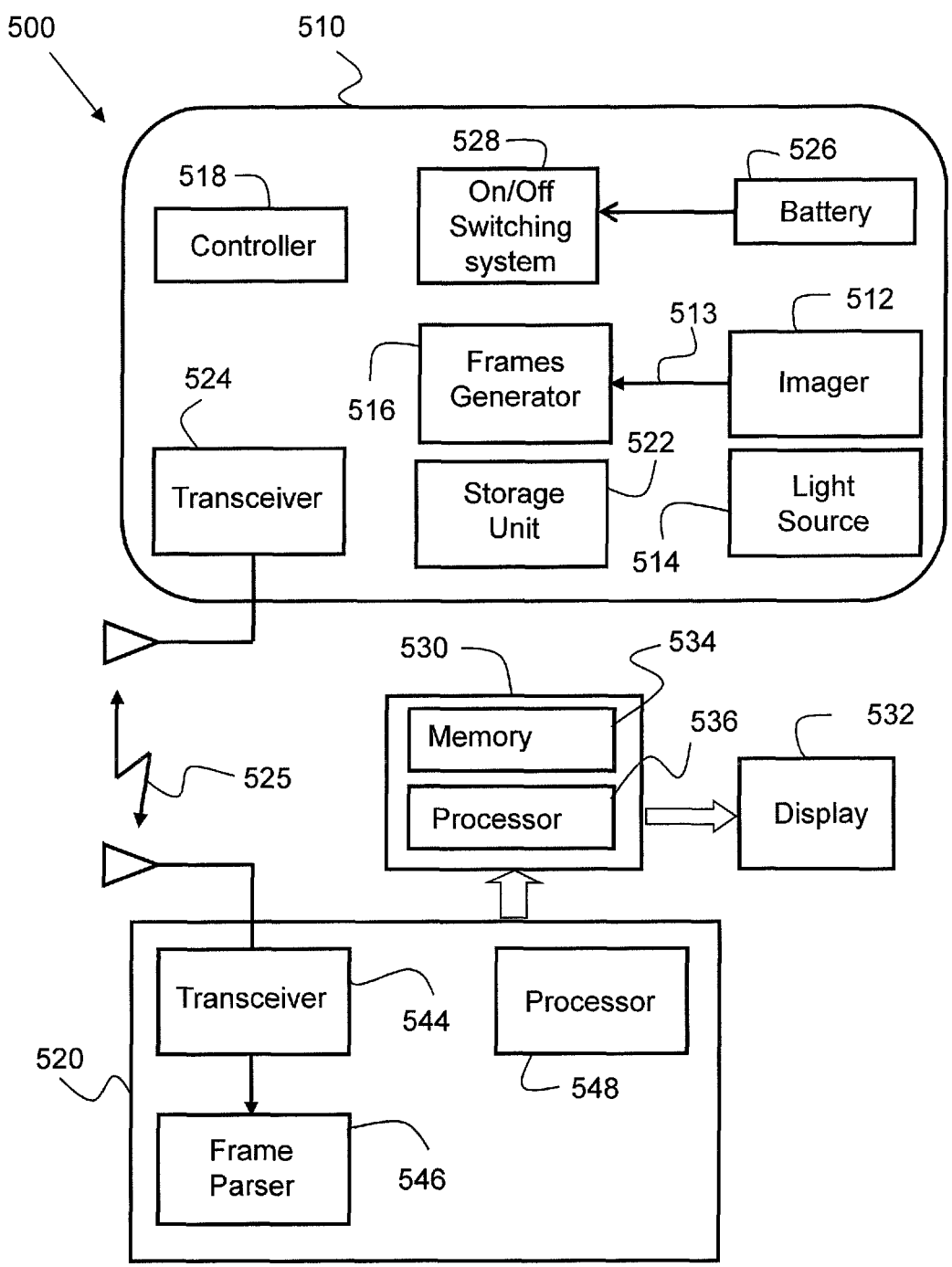
FIG. 5 is a block diagram of an in-vivo imaging system according to an example embodiment.

Any of the "on"/"off" switching systems, embodiments, configurations or switching methodologies disclosed herein, for example in connection with FIGS. 1A-4, may be incorporated into or embedded in, to control the "on"/"off" state of, a swallowable in-vivo, imaging/sensing system, an example of which is shown in FIG. 5, which is described below.

FIG. 5 is a schematic diagram of an in-vivo imaging/sensing system 500 according to an example embodiment of the invention. In-vivo imaging system 500 may include an in-vivo imaging device 510, an external (extra-body) receiver 520 that may function as a data recorder, a workstation 530 (e.g., personal computer), and a display 532. In-vivo imaging device 510 may be, for example a swallowable device, capturing images and transmitting corresponding image frames to an external receiving apparatus (e.g., to receiver 520). The image frames may be presented in real-time or after processing, be combined into an image stream or video movie for display to a user, for example by using display 532.

An in-vivo imaging device may have one or more imagers and/or sensor(s) of other type(s). By way of example, imaging device 510 includes one imager; e.g., imager 512. In-vivo imaging device 510 may also include a light/illumination source 514, a data (e.g., image data or) frame generator 516, a controller 518, a storage unit 522, a transceiver 524, and a power source 526 for powering them. Controller 518, among other things, may controllably operate illumination source 514 to illuminate areas traversed by in-vivo device 510, and coordinates the images capturing timing of imager 512. Controller 518 may momentarily store captured images and related image frames in storage unit 522. Controller 518 may also perform various calculations and store calculation results in storage unit 522.

Frames generator 516 may receive image data 513 from imager 512 and use the image data to produce an image frame ("frame" for short) for the pertinent captured image. Controller 518 may operate illumination source 514 to illuminate, for example, four times per second to enable capturing four images per second, and transceiver 524 to concurrently transmit corresponding frames at the same rate or at a different rate. Controller 518 may operate illumination source 514 to capture more images per second, for example seventeen images per second or any number of images per second that the system can support, and transceiver 524 may concurrently transmit corresponding frames at the same rate. After frames generator 516 produces a frame for a captured image, controller 518 wirelessly communicates 525 the frame to data recorder 520 by using transceiver 524. Receiver 520 may be a stand-alone receiver that is located close enough to the person swallowing the in-vivo device in order to facilitate receiving (and thereafter) processing of the transmitted frames by data recorder 520.

Data recorder 520 may include a transceiver 544 to receive data frames from device 510, a frame parser 546 to parse the frames, and a processor 548 for managing transceiver 544 and frame parser 546. Data recorder 520 may include additional components (e.g., USB interface, Secure Digital ("SD") card driver/interface, controllers, etc.), elements or units, for example, for communicating with (e.g., transferring frames, data, etc. to) an external processing/displaying system that may be configured to process images captured by in-vivo device 510.

In-vivo imaging system 500 may also include a workstation 530. Workstation 530 may include a display or be functionally connected to one an external display, for example to display 532. Workstation 530 may receive image frames, and other types of data from data recorder 520, and present them in real-time, for example as live video, or produce a video stream. Workstation 530 may include a memory 534 for storing frames (and possibly data of other types) transferred from data recorder 520, and a processor 536 for processing the stored data (e.g., image data).

In-vivo imaging device 510 may also include an "on/off" switching system 528 for switching imaging device 510 on and off. "On/off" switching system 528 may be implemented using any of the configurations described in connection with, FIGS. 1A-4. Controller 518 may be configured to function also as controller 320 of FIG. 3, or vice versa. Controller 518 may be part of control unit 121 of FIG. 1A, or part of CLU 120 of FIG. 1B-1D. Part of controller 518 may function as (e.g., it may implement) D-FF 420 of FIG. 4. Transceiver 524 may include CEH unit 103 of FIG. 1A, RFID device 310 of FIG. 3, or RFID device 410 of FIG. 4. Components of in-vivo imaging/sensing system 500 may be similar to components used in a capsule endoscopy system commercially available from the common assignee of the present invention, which capsule endoscopy system is commercially known as the PillCam® capsule, to name a type.

Figure 6A:
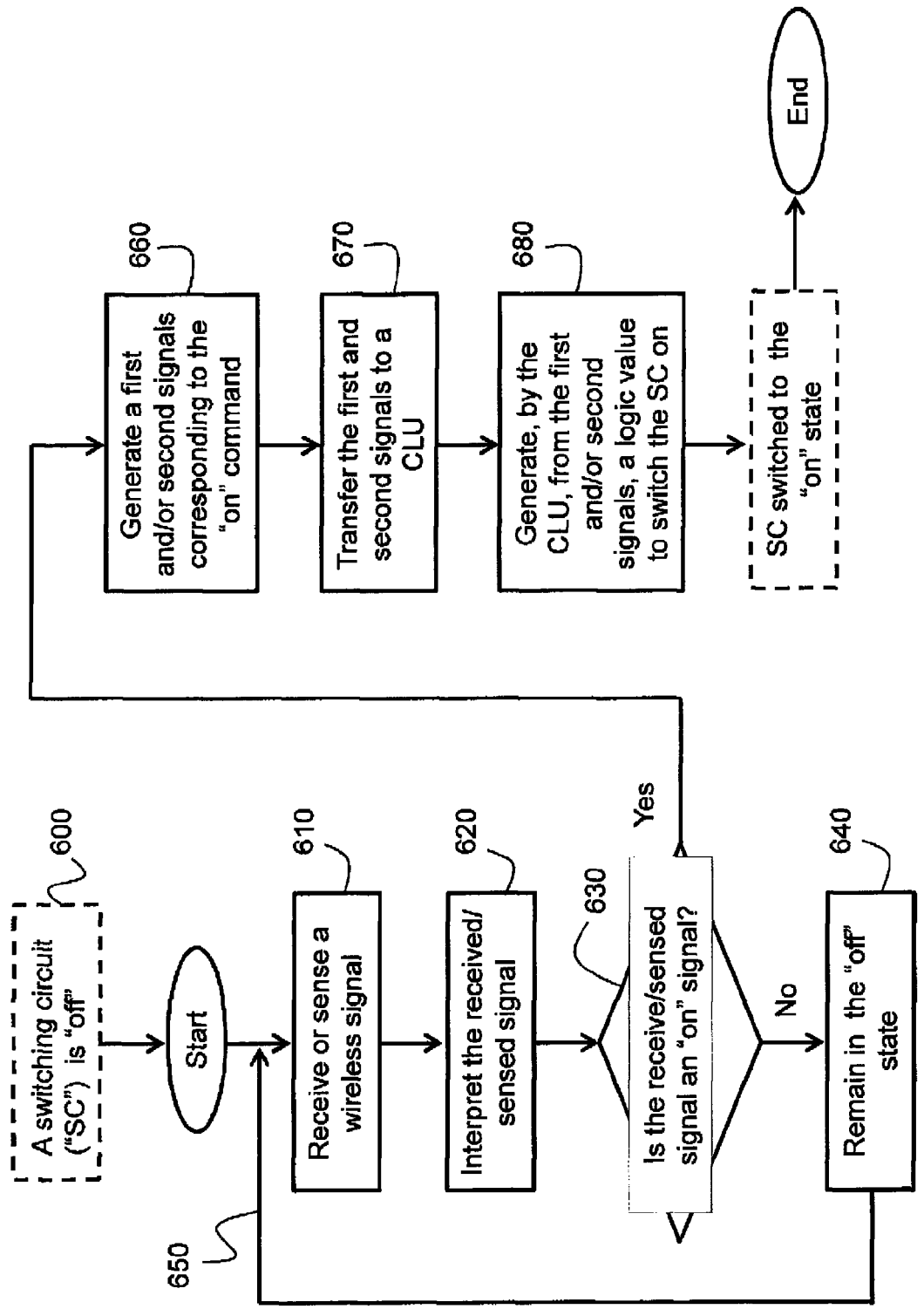
FIG. 6A shows a method for transitioning a switching circuit to the "on" state according to an example embodiment.

FIG. 6A shows a method for transitioning a switching circuit identical or similar to, for example, switching circuit 141 or 130, from "off" state to "on" state, for example to activate an in-vivo sensing system which may initially be shut down (switched off, or deactivated). Assume that the switching circuit (which may be used to turn on and off, for example, a device similar to in-vivo imaging/sensing device 510 of FIG. 5, or another type of device or system), is in the "off" state, as shown at 600.

At step 610, a CEH unit functioning in a similar way as CEH unit 103, 110 or 310, may receive a wireless (e.g., RF) signal, or it may sense a physical parameter (e.g., pressure, acceleration, motion, etc.). At step 620, the CEH unit may interpret the wireless signal, or sensed parameter, as a command to switch the switching circuit "on" or "off". At step 630, the CEH unit may determine whether the wireless signal, or sensed parameter, is a command to switch the switching circuit "on" or "off". If the CEH unit determines, at step 630, that the wireless signal, or sensed parameter, is not a command to switch the switching circuit "on" (the condition is shown as "No" at step 630), the CEH unit may remain in the "off" state (at step 640) and wait (650) and evaluate (620, 630) another wireless signal or sensed parameter, should it receive/sense it (at step 610). However, if the CEH unit determines, at step 630, that the wireless signal, or sensed parameter, is a command to switch the switching circuit "on" (the condition is shown as "Yes" at step 630), the CEH unit may generate and output (at step 660) one signal (according to one embodiment) that represents the "on" command, or two signals (according to another embodiment) that combinatorially represent the "on" command. As described above, in case the CEH unit generates two signals, one of the two signals may conditionally initiate a transition of the switching circuit from "off" state to "on" state, the condition may be that the second signal has the characteristics (e.g., shape, logic value, timing, etc.) required to actually perform, or force, the transition. At step 670, the CEH unit may transfer the one signal (or two signals) to a CLU functioning in a similar way as CLU 102, 120 or 310. At step 680, the CLU may generate, from the first and/or second signals, a logic value to switch the switching circuit on.

The switching method described in connection with FIG. 6A may be used by a device such as a swallowable in-vivo imaging, or otherwise sensing, capsule shown, for example, in FIG. 5.

Figure 6B:
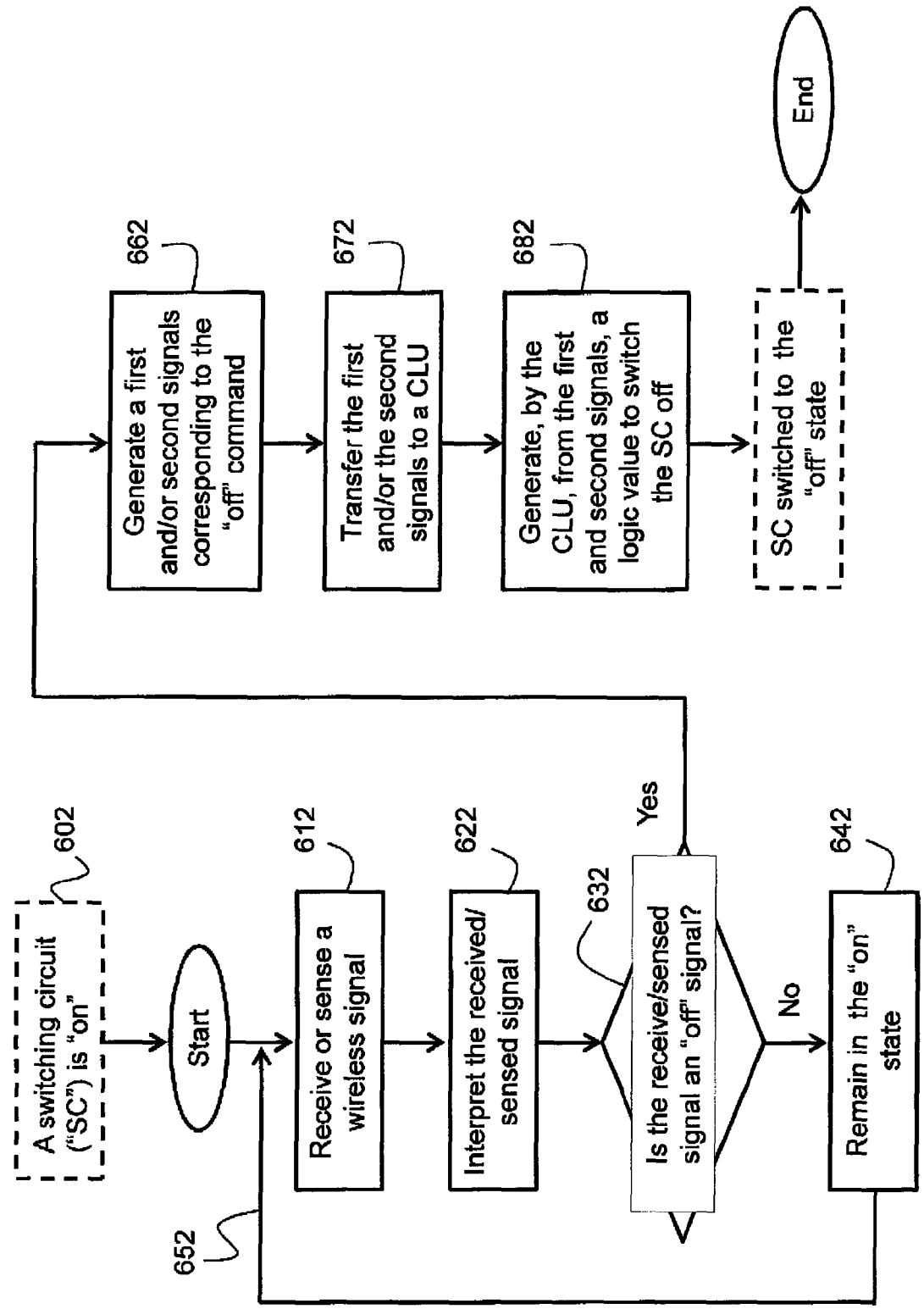
FIG. 6B shows a method for transitioning a switching circuit to the "off" state according to an example embodiment.

FIG. 6B shows a method according to one embodiment for transitioning a switching circuit identical or similar to, for example, switching circuit 141 or 130, from "on" state to "off" state, for example to deactivate an in-vivo sensing system which is initially switched on, or activated. Assume that the switching circuit (which may be used to turn on and off, for example, an in-vivo imaging/sensing device similar to the device shown in FIG. 5, or another type of device or system), is in the "on" state (this is shown at 602).

At step 612, a CEH unit functioning in a similar way as CEH unit 103, 110 or 310, may receive a wireless (e.g., RF) signal, or sense a physical parameter (e.g., motion). At step 622 the CEH unit may interpret the wireless signal, or sensed parameter, as a command to switch the switching circuit "on" or "off". At step 632, the CEH unit may determine whether the wireless signal, or sensed parameter, is a command to switch the switching circuit "on" or "off". If the CEH unit determines, at step 632, that the wireless signal, or sensed parameter, is not a command to switch the switching circuit "off" (the condition is shown as "No" at step 632), the CEH unit may remain in the "on" state (at step 642) and wait (652) and evaluate (622, 632) another wireless signal or sensed parameter, should it receive/sense it (at step 612). However, if the CEH unit determines, at step 632, that the wireless signal, or sensed parameter, is a command to switch the switching circuit "off" (the condition is shown as "Yes" at step 632), the CEH unit may generate and output (at step 662) one signal (according to one embodiment) that represents the "off" command, or two signals (according to another embodiment) that combinatorially represent the "off" command. As described above, in case the CEH unit generates two signals, one of the two signals may conditionally initiate a transition of the switching circuit from "on" state to "off" state, the condition may be that the second signal has the characteristics (e.g., shape, logic value, timing, etc.) required to actually perform the transition. At step 672, the CEH unit may transfer the one signal (or two signals) to a CLU functioning in a similar way as CLU 102, 120 or 310. At step 682, the CLU may generate, from the first and/or second signals, a logic value to switch the switching circuit off.

The switching method described in connection with FIG. 6B may be used by a device such as a swallowable in-vivo imaging, or otherwise sensing, capsule shown, for example, in FIG. 5.

Figure 7A:
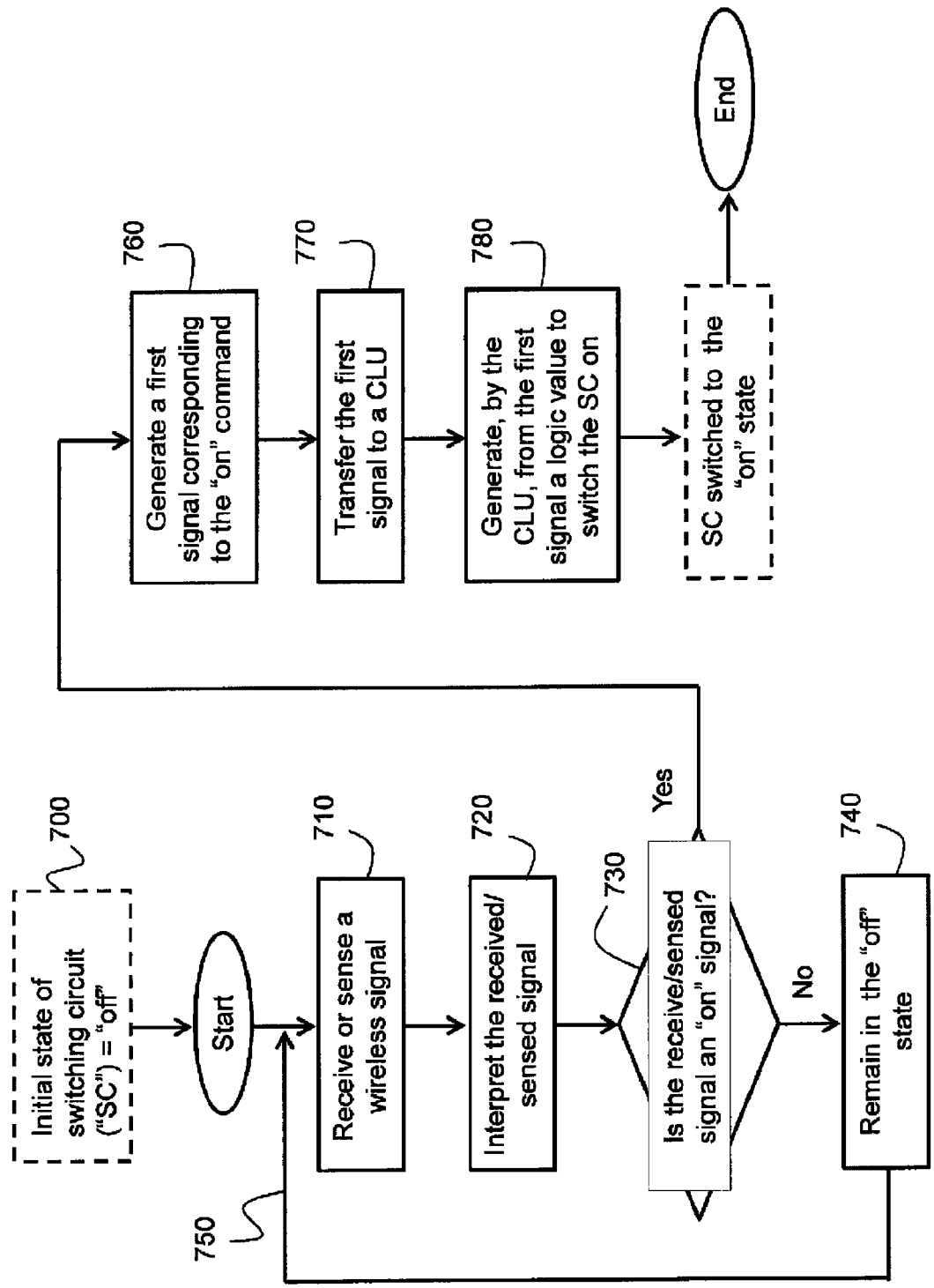
FIG. 7A shows a method for transitioning a switching circuit to the "on" state according to another example embodiment.

FIG. 7A shows one embodiment of a method for transitioning a switching circuit identical or similar to, for example, switching circuit 141 or 130, from "off" state to "on" state, for example to activate an in-vivo sensing system which is initially shut down (switched off, or deactivated). Assume that the switching circuit (which may be used to turn on and off, for example, an in-vivo imaging/sensing device similar to the device shown in FIG. 5, or another type of device or system), is in the "off" state (this is shown at 700).

At 710, a CEH unit functioning in a similar way as CEH unit 103, 110 or 310, may receive a wireless (e.g., RF) signal, or sense a physical parameter (e.g., motion). At step 720, the CEH unit may interpret the wireless signal, or sensed parameter, as a command to switch the switching circuit "on" or "off". At step 730, the CEH unit may determine whether the wireless signal, or sensed parameter, is a command to switch the switching circuit "on" or "off". If the CEH unit determines, at step 730, that the wireless signal, or sensed parameter, is not a command to switch the switching circuit "on" (the condition is shown as "No" at step 730), the CEH unit may remain in the "off" state (at step 740) and wait (750) and evaluate (720, 730) another wireless signal or sensed parameter, should it receive/sense it (at step 710). However, if the CEH unit determines, at step 730, that the wireless signal, or sensed parameter, is a command to switch the switching circuit "on" (the condition is shown as "Yes" at step 730), the CEH unit may generate and output (at step 760) a first signal representing the "on" command. At step 770, the CEH unit may transfer the first signal to a CLU functioning in a similar way as CLU 102, 120 or 310. At step 780, the CLU may generate, from the first signal, a logic value to switch the switching circuit on.

The switching method described in connection with FIG. 7A may be used by a device such as a swallowable in-vivo imaging, or otherwise sensing, capsule shown, for example, in FIG. 5.

Figure 7B:
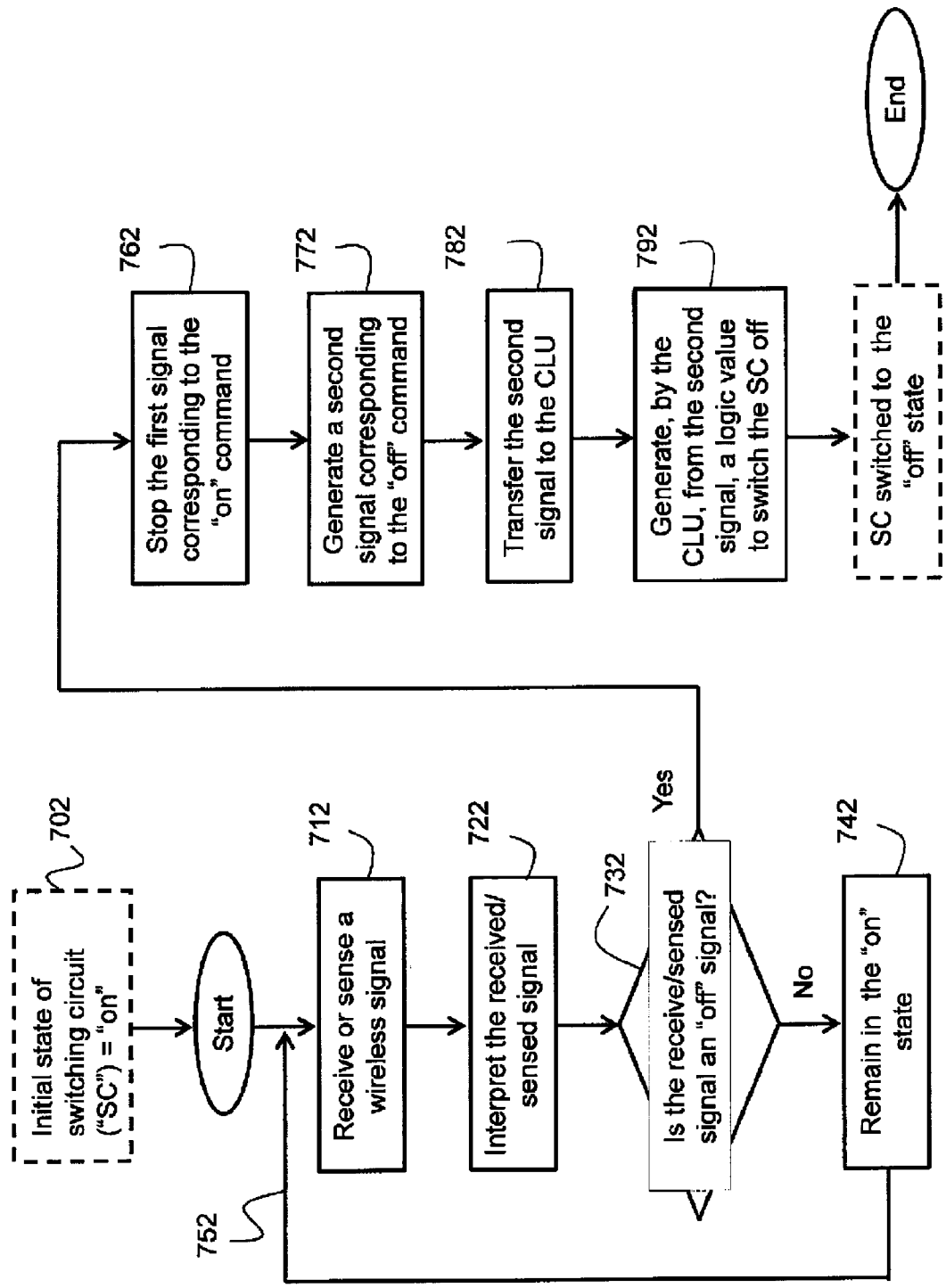
FIG. 7B shows a method for transitioning a switching circuit to the "off" state according to another example embodiment.

FIG. 7B shows one embodiment of a method for transitioning a switching circuit identical or similar to, for example, switching circuit 141 or 130, from "on" state to "off" state, for example to activate an in-vivo sensing system which is initially switched on, or activated. Assume that the switching circuit (which may be used to turn on and off, for example, an in-vivo imaging/sensing device similar to the device shown in FIG. 5, or another type of device or system), is in the "on" state (this is shown at 702).

At 712, a CEH unit functioning in a similar way as CEH unit 103, 110 or 310, may receive a wireless (e.g., RF) signal, or sense a physical parameter (e.g., motion). At step 722, the CEH unit may interpret the wireless signal, or sensed parameter, as a command to switch the switching circuit "on" or "off". At step 732, the CEH unit may determine whether the wireless signal, or sensed parameter, is a command to switch the switching circuit "on" or "off". If the CEH unit determines, at step 732, that the wireless signal, or sensed parameter, is not a command to switch the switching circuit "off" (the condition is shown as "No" at step 732), the CEH unit may remain in the "on" state (at step 742) and wait (752) and evaluate (722, 732) another wireless signal or sensed parameter, should it receive/sense it (at step 712). However, if the CEH unit determines, at step 732, that the wireless signal, or sensed parameter, is a command to switch the switching circuit "off" (the condition is shown as "Yes" at step 732), the CEH unit may disable, at step 762, the first signal used by the CEH unit to switch the switching circuit "on" (as per step 760 of FIG. 7A), and generate, at step 772, a second signal representing the "off" command.

At step 782, the CEH unit may transfer the second signal to a CLU functioning in a similar way as CLU 102, 120 or 310. At step 792, the CLU may generate, from the second signal, a logic value to switch the switching circuit off.

The switching method described in connection with FIG. 7B may be used by a device such as a swallowable in-vivo imaging, or otherwise sensing, capsule shown, for example, in FIG. 5.

Changes in a physical parameter (e.g., directional acceleration) sensed by the CEH unit may be interpreted as the "on" signal or command, or as the "off" signal or command. For example, an acceleration sensed by the CEH unit (e.g., by the transducer) in a particular direction with respect to the device whose on/off state is controlled may be interpreted by the CEH's controller as the "on" signal or command, and an acceleration sensed by the CEH unit in another direction may be interpreted as the "off" signal or command. In another example, a particular pattern of a physical parameter (e.g., a pressure changing in a particular pattern) may be interpreted as the "on" signal/command (or as the "off" signal/command), and a different pattern of the physical parameter (e.g., the pressure changing in a different way) may be interpreted as the "off" signal/command (or as the "off" signal/command).

The articles "a" and "an" are used herein to refer to one or to more than one (e.g., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to". Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. Features of certain embodiments may be used with other embodiments shown herein. The present disclosure is relevant to various types of in-vivo devices (e.g., in-vivo devices with one or more imagers, -vivo devices with no imagers at all, etc.). Hence the scope of the claims that follow is not limited by the disclosure herein.

The invention claimed is:
1. A method for controlling an on/off state of a switching circuit comprising a power input terminal connected to a power source, a power output terminal connected to a load and a control input, the method comprising:
    sensing a wireless signal or physical parameter by a first unit of a control circuit, the first unit capable of outputting a first digital signal and a second digital signal;

interpreting, by the first unit, the wireless signal or physical parameter either as an "on" signal to transition the switching circuit to an "on" state in which the power input terminal is connected to the power output terminal of the switching circuit, or as an "off" signal to transition the switching circuit to the "off" state in which the power input terminal is disconnected from the power output terminal of the switching circuit;

transferring, from the first unit to a second unit, one of: the first digital signal congruent with an "on" signal; the second digital signal congruent with an "off" signal; and both the first digital signal and the second digital signal which combinatorially are congruent with the "on" signal or "off" signal;

providing, by the second unit, an output logic value to the control input of the switching circuit as a function of the first digital signal or the second digital signal, or both digital signals; and transitioning the switching circuit to the "on" state or to the "off" state according to the output logic value provided to the control input of the switching circuit.

2. The control method as in claim 1, wherein the first digital signal and the second digital signal are respectively congruent with the "on" state and "off" state.

3. The control method as in claim 1, comprising harvesting, by the first unit, electrical energy from the sensed wireless signal or sensed physical parameter to initially power up the first unit and/or the second unit.

4. The control method as in claim 1, wherein the first digital signal comprises energy harvested from the sensed wireless signal or sensed physical parameter, and wherein the second digital signal comprises a signal indicative of internal data writing in the first unit.

5. The control method as in claim 1, comprising:
providing the first digital signal to a logic unit of the second unit to transition the switching circuit to the "on" state; and
providing the second digital signal to a control unit of the second unit to transition the switching circuit to the "off" state.

6. The control method as in claim 1, wherein the second unit comprises a "D" type flip-flop (D-FF) circuit, the method comprising,
transitioning the switching circuit to the "on" state by providing a logic value corresponding to the "on" state to a data (D) input of the D-FF and a clock pulse to a clock (CLK) input of the D-FF; or
transitioning the switching circuit to the "off" state by providing a logic value corresponding to the "off" state to the D input of the D-FF and a clock pulse to the CLK input of the D-FF.

7. The control method as in claim 1, comprising transferring the first digital signal and/or the second digital signal from the first unit to the second unit by using a wired communication protocol.

8. The control method as in claim 7, wherein the wired communication protocol is the IIC protocol.

9. A control circuit for controlling a state of a switching circuit comprising a power input terminal connected to a power source, a power output terminal connected to a load and a control input terminal, the control circuit comprising:
a first unit, the first unit capable of outputting a first digital signal and a second digital signal and configured to:
sense and interpret a wireless signal or physical parameter either as an "on" signal to transition the switching circuit to an "on" state in which the power input terminal and the power output terminal of the switching circuit are connected, or as an "off" signal to transition the switching circuit to the "off" state in which the power input terminal is disconnected from the power output terminal, and
output one of a first digital signal congruent with an "on" signal; a second digital signal congruent with an "off" signal; and both the first digital signal and the second digital signal which combinatorially are congruent with the "on" signal or "off" signal; and
a second unit configured to provide to said control input a logic value congruent with the state to which the switching circuit is to be transitioned, wherein the logic value is a function of the first digital signal, or the second digital signal, or both digital signals.

10. The control circuit as in claim 9, wherein the first unit comprises:
a communication and energy harvesting unit comprising a transducer to sense the wireless signal and/or the physical parameter;
a first output port and a second output port; and
a controller configured to interpret the sensed wireless signal or physical parameter, and to output the first digital signal or the second digital signal, or both digital signals, via the first and second outputs according to the interpretation.

11. The control circuit as in claim 10, wherein the communication and energy harvesting unit is to harvest electrical energy from the sensed wireless signal or physical parameter to initially power up the first unit and/or the second unit.

12. The control circuit as in claim 10, wherein the second unit comprises:
a control unit comprising an input connected to one of the first and second output ports of the first unit, and an output; and
a logic unit having a first input connected to the output of the control unit, and a second input connected to the other one of the first and second output ports of the first unit.

13. The control circuit as in claim 12, wherein the controller of the first unit is configured to transition the switching circuit to the "on" state and to the "off" state by providing a different combination of the first digital signal and the second digital signal to the control unit, or to the control unit and logic unit.

14. The control circuit as in claim 9, wherein the first unit comprises radio frequency identification ("RFID") device.

15. The control circuit as in claim 14, wherein the first digital signal comprises an electrical energy harvested by the RFID device, and wherein the second digital signal comprises a signal indicative of data writing inside the RFID device.

16. The control circuit as in claim 9, wherein the second unit comprises a "D" type flip-flop (D-FF) circuit, and wherein the controller of the first unit is configured to transition the switching circuit to the "on" state by providing a first logic value corresponding to the "on" state to a data (D) input of the D-FF and a clock pulse to a clock (CLK) input of the D-FF to set the Q output of the D-FF to the first logic value, and to the "off" state by providing a second logic value corresponding to the "off" state to the D input of the D-FF and a clock pulse to the CLK input of the D-FF to set the Q output of the D-FF to the second logic value.

17. The control circuit as in claim 9, wherein the controller is to transfer the first digital signal, or the second digital signal, or both signals to the second unit using a wired communication protocol.

* * * * *